(12) United States Patent
Huttemann et al.

(10) Patent No.: US 10,071,261 B2
(45) Date of Patent: *Sep. 11, 2018

(54) LIGHT THERAPY TREATMENT

(71) Applicant: Wayne State University, Detroit, MI (US)

(72) Inventors: Maik Huttemann, Grosse Pointe Park, MI (US); Thomas Sanderson, Plymouth, MI (US); John Kamholz, Coralville, IA (US); Kwaku Nantwi, Toledo, OH (US); Karin Przyklenk, Grosse Pointe Park, MI (US); Icksoo Lee, Cheonan-Si (KR); Lawrence Grossman, Ann Arbor, MI (US)

(73) Assignee: Wayne State University, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/709,869

(22) Filed: May 12, 2015

(65) Prior Publication Data

US 2015/0246240 A1    Sep. 3, 2015

Related U.S. Application Data

(60) Continuation-in-part of application No. 14/473,105, filed on Aug. 29, 2014, which is a division of application No. 12/771,137, filed on Apr. 30, 2010, now Pat. No. 8,945,196.

(60) Provisional application No. 61/215,105, filed on May 1, 2009.

(51) Int. Cl.
*A61N 5/06*    (2006.01)

(52) U.S. Cl.
CPC .............. *A61N 5/06* (2013.01); *A61N 5/0613* (2013.01); *A61N 2005/0626* (2013.01); *A61N 2005/0643* (2013.01); *A61N 2005/0647* (2013.01); *A61N 2005/0652* (2013.01); *A61N 2005/0659* (2013.01)

(58) Field of Classification Search
USPC ...................................... 606/2, 3; 607/88, 89
See application file for complete search history.

(56) References Cited

U.S. PATENT DOCUMENTS

| | | | |
|---|---|---|---|
| 4,930,504 A | 6/1990 | Diamantopoulos et al. | |
| 4,966,144 A | 10/1990 | Rochkind et al. | |
| 5,259,380 A | 11/1993 | Mendes et al. | |
| 5,464,436 A | 11/1995 | Smith | |
| 5,616,140 A | 4/1997 | Prescott | |
| 5,989,245 A | 11/1999 | Prescott | |

(Continued)

FOREIGN PATENT DOCUMENTS

| | | |
|---|---|---|
| EP | 0130950 A2 | 1/1985 |
| WO | WO-2009117323 A2 | 9/2009 |

OTHER PUBLICATIONS

International Search Report for PCT/US2010/033175 dated Jul. 23, 2010.

(Continued)

*Primary Examiner* — Tod T Van Roy

(57) ABSTRACT

A light therapy method, comprising identifying a pathological condition in a patient, selecting at least one light wavelength based on the identified pathological condition, and applying one or a combination of the selected light wavelengths to the patient using a light source.

67 Claims, 11 Drawing Sheets

(56) References Cited

U.S. PATENT DOCUMENTS

| | | | |
|---|---|---|---|
| 6,024,739 A * | 2/2000 | Ponzi | A61B 18/24 |
| | | | 600/374 |
| 6,214,035 B1 | 4/2001 | Streeter | |
| 6,267,780 B1 | 7/2001 | Streeter | |
| 6,273,905 B1 | 8/2001 | Streeter | |
| 6,290,714 B1 | 9/2001 | Streeter | |
| 6,312,451 B1 | 11/2001 | Streeter | |
| 6,395,016 B1 | 5/2002 | Oron et al. | |
| 6,443,974 B1 | 9/2002 | Oron et al. | |
| 6,537,304 B1 | 3/2003 | Oron | |
| 6,690,958 B1 | 2/2004 | Walker et al. | |
| 6,918,922 B2 | 7/2005 | Oron | |
| 7,051,738 B2 | 5/2006 | Oron et al. | |
| 7,107,997 B1 | 9/2006 | Moses et al. | |
| 7,303,578 B2 | 12/2007 | De Taboada et al. | |
| 7,309,348 B2 | 12/2007 | Streeter et al. | |
| 7,316,922 B2 | 1/2008 | Streeter | |
| 7,344,555 B2 | 3/2008 | Anders et al. | |
| 7,351,253 B2 | 4/2008 | DiMauro et al. | |
| 7,354,432 B2 | 4/2008 | Eells et al. | |
| 7,447,919 B2 | 11/2008 | Liepe et al. | |
| 7,534,255 B1 | 5/2009 | Streeter et al. | |
| 7,575,589 B2 | 8/2009 | De Taboada et al. | |
| 8,504,130 B2 | 8/2013 | Gonopolskiy et al. | |
| 2002/0068927 A1 | 6/2002 | Prescott | |
| 2002/0183809 A1 | 12/2002 | Oron et al. | |
| 2003/0004499 A1 | 1/2003 | McDaniel | |
| 2003/0109906 A1 | 6/2003 | Streeter | |
| 2003/0181962 A1 | 9/2003 | Streeter | |
| 2003/0212442 A1 | 11/2003 | Streeter | |
| 2003/0216797 A1 | 11/2003 | Oron | |
| 2004/0039269 A1 | 2/2004 | Ward et al. | |
| 2004/0153130 A1 | 8/2004 | Oron et al. | |
| 2004/0210275 A1 | 10/2004 | Town et al. | |
| 2004/0220513 A1 | 11/2004 | Streeter | |
| 2004/0260367 A1 | 12/2004 | De Taboada et al. | |
| 2005/0019744 A1 | 1/2005 | Bertuglia | |
| 2005/0020595 A1 | 1/2005 | Kalish et al. | |
| 2005/0107851 A1 | 5/2005 | Taboada et al. | |
| 2005/0171414 A1 | 8/2005 | Demos et al. | |
| 2005/0197681 A1 | 9/2005 | Barolet et al. | |
| 2006/0064504 A1 | 3/2006 | Rechterman et al. | |
| 2006/0217787 A1 | 9/2006 | Olson et al. | |
| 2006/0241726 A1 | 10/2006 | Whitehurst | |
| 2006/0253177 A1 | 11/2006 | Taboada et al. | |
| 2007/0038269 A1 | 2/2007 | Whitehurst | |
| 2007/0073366 A1 | 3/2007 | Porco | |
| 2007/0179570 A1 | 8/2007 | De Taboada et al. | |
| 2007/0179571 A1 | 8/2007 | De Taboada et al. | |
| 2008/0009689 A1 | 1/2008 | Benaron et al. | |
| 2008/0033412 A1 | 2/2008 | Whelan et al. | |
| 2008/0058881 A1 | 3/2008 | Wagner et al. | |
| 2008/0070229 A1 | 3/2008 | Streeter | |
| 2008/0131968 A1 | 6/2008 | Bornstein | |
| 2008/0139908 A1 | 6/2008 | Kurth | |
| 2008/0139992 A1 | 6/2008 | Bornstein | |
| 2009/0216301 A1 | 8/2009 | Streeter et al. | |
| 2009/0254154 A1 | 10/2009 | De Taboada et al. | |
| 2009/0299441 A1 | 12/2009 | Bornstein | |
| 2010/0087719 A1 | 4/2010 | Benni | |
| 2011/0066213 A1 | 3/2011 | Huttermann et al. | |

OTHER PUBLICATIONS

Lassmann, Hans et al., "Heterogeneity of multiple sclerosis pathogenesis: implications for diagnosis and therapy," TRENDS in Molecular Medicine vol. 7 No. 3, Mar. 3, 2001, pp. 115-121.

Soulika, Athena M. et al., "Initiation and Progression of Axonopathy in Experimental Autoimmune Encephalomyelitis," The Journal of Neuroscience, Nov. 25, 2009 • 29(47):14965-14979.

Goshgarian, Harry G., "Invited Review: The crossed phrenic phenomenon: a modelfor plasticity in the respiratory pathways following spinal cord injury," J Appl Physiol 94:795-810, 2003.doi:10.1152/japplphysiol.00847.2002.

* cited by examiner

LIGHT THERAPY TREATMENT

CROSS-REFERENCE TO RELATED APPLICATIONS

This application is a continuation-in-part of, and claims priority to, U.S. application Ser. No. 14/473,105 filed on Aug. 29, 2014, which is a divisional of U.S. application Ser. No. 12/771,137 filed Apr. 30, 2010 and issued as U.S. Pat. No. 8,945,196 on Feb. 3, 2015, which claims the benefit of U.S. Application Ser. No. 61/215,105 filed on May 1, 2009, the contents of which are incorporated herein in their entirety.

BACKGROUND

An ischemic event occurs when the supply of oxygen and nutrients to an organ or tissue is restricted. For example, interruption of blood flow to regions of the brain and heart results in myocardial and cerebral ischemia, respectively. Timely restoration of oxygen and nutrients, termed reperfusion, is essential for the survival of the ischemic organ or tissue. However, despite the benefits of this reintroduction of oxygen to ischemic tissue, reperfusion per se can also precipitate tissue death. The mechanisms of this phenomenon, termed reperfusion injury, are complex but involve the formation of cytotoxic oxygen-derived free radicals also called reactive oxygen species (ROS) that can exacerbate death and dysfunction of previously ischemic tissue. Accordingly, an apparatus and method that limit the production of ROS during reperfusion, and thus attenuating reperfusion injury and maximizing the benefits of timely reperfusion is needed.

DETAILED DESCRIPTION

Figure 1:
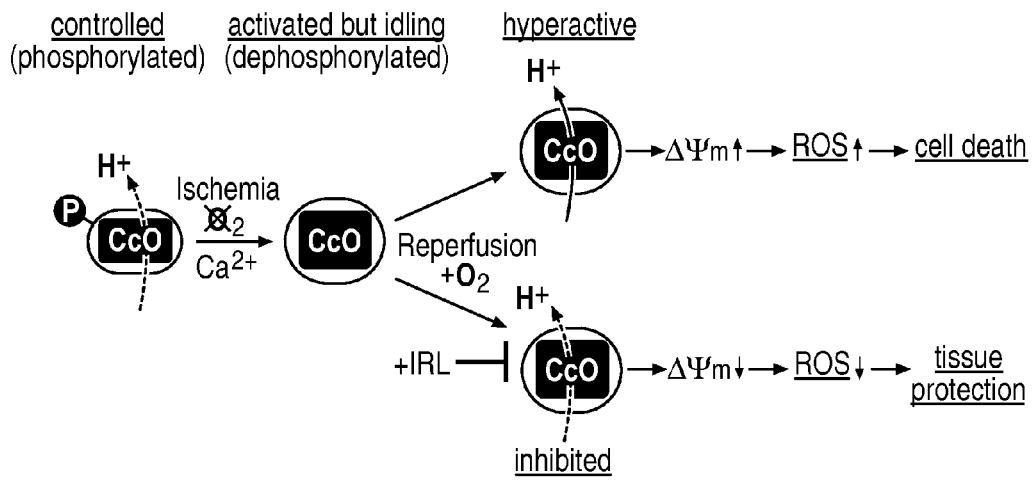
FIG. 1 illustrates an exemplary model of tissue protection through inhibition of cytochrome c oxidase (CcO) with infrared light during reperfusion.

Many disease conditions, both acute and chronic, involve the formation of cytotoxic oxygen-derived reactive oxygen species (ROS) that can cause cell dysfunction and death. The majority of ROS are generated in the mitochondria under conditions of cellular stress. Studies have shown that ROS are produced at high mitochondrial membrane potentials. The mitochondrial membrane potential is generated by electron transport chain complexes, one of which is cytochrome c oxidase (CcO), the proposed rate-limiting and thus key enzyme in vivo. Conditions of cellular stress lead to an increase in the activity of CcO through changes in posttranslational modifications of CcO, which causes pathologically high mitochondrial membrane potentials. This in turn leads to excessive ROS production and cellular demise. Accordingly, a therapeutic approach is needed that limits the production of ROS during cellular stress.

Four wavelengths of infrared light (IRL) have been identified that directly affect CcO and reduce CcO activity. CcO transfers electrons from cytochrome c to molecular oxygen and contains three copper ions per monomer that absorb IRL. All three coppers are located at central sites within the CcO enzyme, the binuclear ("copper A") site, located at the entry point for electrons, and the other ("copper B") site, which is part of the catalytic pocket that binds oxygen.

IRL can be applied in a non-invasive manner to cells and tissues facing stress. An advantage over pharmacological treatments is that the delivery of IRL does not depend on blood flow and that it works immediately upon initialization.

IRL treatment leads to profound tissue protection in adult animal models of ischemia/reperfusion injury of the brain and heart.

The treatment described herein may be used to limit the production of ROS or reactive oxygen and nitrogen species generated during, for example, reoxygenation or reperfusion of ischemic tissue. As described herein, ischemia is defined as the restriction of oxygen and nutrients to an organ or tissue. Reperfusion is defined as the process where oxygen and other nutrients are restored to ischemic tissue. The onset of reperfusion is defined as the instant in which reperfusion begins either naturally or as a result of clinical intervention. By applying the disclosed treatment at before, during, and/or after reoxygenation (e.g., prior to and during the initial minutes-hours of reperfusion) cell death and cell damage are reduced that are caused by, for instance, reperfusion injury following an ischemic event.

Accordingly, an exemplary process includes applying light to an ischemic area of tissue before reperfusion and during the initial minutes-hours of reperfusion. The onset of reperfusion may be initiated by clinical intervention such as administering a clot-busting drug, inflating/deflating an angioplasty balloon, resuscitation, transfusion, or administering vaso-active drugs, among others.

In another approach, exemplary processes include applying light to an ischemic area of tissue before, during, and/or after the initiation of clinical intervention following an ischemic event. In one example, according to the disclosure, treatment may be for neonatal hypoxia/ischemia (premature or at term) when oxygen compromise is suspected. In another example, treatment may be for multiple sclerosis (MS). In still another example, treatment may be for spinal cord injury.

In any event, applying light with the appropriate wavelength or wavelengths to the ischemic area at the appropriate time or times directly or indirectly inhibits cytochrome c oxidase (CcO, sometimes also abbreviated as COX). As discussed in greater detail below, this direct or indirect inhibition of CcO indirectly reduces the production of ROS, resulting in reduced cell damage and cell death caused by reperfusion injury. It is possible that another mechanism besides inhibiting CcO causes the reduction in ROS production. Moreover, multiple mechanisms, of which reducing CcO activity may be one, could be responsible for reduced ROS production. For instance, the treatment described herein may inhibit the terminal step of an electron transport chain (i.e., the electron transfer from cytochrome c to CcO to molecular oxygen). Further, the treatment described herein may result in other benefits in addition to or besides the reduction of ROS.

Organs in the body depend on aerobic energy provided by the mitochondrial oxidative phosphorylation process (OxPhos). In instances of myocardial ischemia, cerebral ischemia, and other instances where blood supply and/or oxygen is reduced in tissue, energy is depleted in the affected areas. Cellular response to this stressed situation includes the release of calcium, leading to activation of mitochondrial proteins, likely mediated through protein dephosphorylation. However, during ischemia, OxPhos cannot proceed due to the lack of its terminal substrate, oxygen. Upon reperfusion, oxygen and other nutrients reach the stressed mitochondria. However, a substantial fraction of cellular damage occurs at the onset of reperfusion due to hyperactive OxPhos enzymes. Namely, while attempting to restore energy levels, OxPhos complexes generate pathologically high mitochondrial membrane potentials (i.e., a transient hyperpolarization of the mitochondrial membrane potential), a condition known to lead to the excessive production of ROS. ROS trigger cellular death processes during reperfusion, thus producing extensive damage to the affected tissues. Accordingly, the treatment described herein may be used to modulate mitochondrial function in vivo and limit the production of ROS during reperfusion of tissue, such as the heart or brain.

In one exemplary approach, mitochondrial function may be modulated by down-regulation of OxPhos through non-pharmacological inhibition of the OxPhos step catalyzed by CcO, i.e., the electron transfer from cytochrome c to CcO to oxygen, using infrared light. This non-invasive modulation of OxPhos using infrared light may protect tissues, such as the heart or brain, from ischemia and/or reperfusion injury. Moreover, the direct or indirect inhibition of CcO may reduce the mitochondrial membrane potential during reperfusion and subsequently attenuate reperfusion-induced ROS generation, which is a likely underlying mechanism for infrared light mediated cardio- and neuro-protection.

Studies have shown that cardiovascular and cerebrovascular disease, including cardiac ischemia as a consequence of acute myocardial infarction and brain ischemia resulting from cardiac arrest or stroke, remain leading causes of death and disability. Established treatments to limit tissue damage caused by myocardial and cerebral ischemia include promptly restoring oxygen delivery to the ischemic areas. However, while timely reflow helps salvage ischemic cells including cardiomyocytes and neurons, reperfusion can also precipitate significant, irreversible tissue damage, and thus offset some of the benefits of reperfusion. Moreover, reperfusion can contribute to death and disability following acute myocardial infarction, stroke, and resuscitation/return of spontaneous circulation.

Previous attempts to attenuate myocardial ischemia-reperfusion injury in the heart and brain have focused on pharmacological therapies to scavenge ROS. These pharmacological therapies have yielded inconsistent results in experimental models and have failed to translate into clinical therapies. Previous attempts to use light therapy following an ischemic event were not effective because the light in the previous treatments was applied at the wrong time and had a wavelength that increased CcO activity, which may have caused further cell damage and death. That is, the previous attempts were not effective because the wavelengths applied were not based on wavelengths that inhibit CcO activity, or provide other benefits that can be obtained when using light having wavelengths that fall within the disclosed ranges of light wavelengths.

To the contrary, the exemplary treatment described herein reduces the production of ROS rather than only scavenging ROS. Specifically, when the appropriate wavelengths of light are selected and when the light is applied at the appropriate time relative to reoxygenation, infrared light treatment reduces infarct size following acute myocardial infarction and reduce the extent of neurological deficits following brain ischemia.

A main photoacceptor of infrared light is mitochondrial CcO. Dimeric CcO is a 26-subunit enzyme that can adjust energy production to demand and is regulated by phosphorylation and the cellular ATP/ADP ratio (as commonly known, ATP refers to adenosine triphosphate and ADP refers to adenosine diphosphate). CcO is the terminal enzyme and proposed rate-limiting complex of the mammalian electron transport chain under physiological conditions. CcO contains several chromophores, including two copper and two heme centers, that are involved in enzyme catalysis and function as the primary photoacceptors for infrared light. In addition, amino acids involved in proton pumping may also be photomodulated. Cytochrome c, which delivers electrons to CcO and contains a heme group that may also be a photoacceptor of infrared light and may contribute to the overall effect on CcO activity.

CcO responds differently to different wavelengths of infrared light. Indeed, wavelengths of light that directly or indirectly inhibit CcO are identified, which in turn indirectly reduces production of ROS. One way to identify wavelengths of light that inhibit CcO is to scan the near infrared wavelengths and, in parallel, analyze the effect on CcO activity. A treatment that incorporates the wavelengths identified to inhibit CcO may also inhibit respiration in a reversible and switch-like manner.

One mechanism regulating the activity of the electron transport chain complexes is via the mitochondrial membrane potential. When the mitochondrial membrane potential is high, further proton pumping is inhibited. A decrease in the mitochondrial membrane potential through proton utilization by ATP synthase may allow the electron transport chain to pump protons. As an extension to that classical model, the cell signaling pathways also control the activity of the electron transport chain complexes. This in turn controls the mitochondrial membrane potential, maintaining healthy, intermediate mitochondrial membrane potential levels between, for instance, 80-140 mV. Such regulation helps higher organisms because the mitochondrial membrane potential is directly related to the production of ROS. When the mitochondrial membrane potential is greater than, for instance, 140 mV, ROS production increases exponentially. Mitochondria of resting cells with healthy or intermediate mitochondrial membrane potential levels do not produce significant amounts of ROS. Thus, the maintenance of physiologically intermediate mitochondrial membrane potential values avoids excess generation of ROS but provides the capability to produce ATP because maximal rates of ATP synthesis by ATP synthase occur when mitochondrial membrane potential levels are, for instance, between 100 and 120 mV.

Stress conditions such as ischemia lead to the release of calcium, disruption of mitochondrial function, differential phosphorylation, and especially dephosphorylation of many mitochondrial proteins, which may be mediated by calcium-activated phosphatases and which can lead to cell death. Referring to FIG. 1, during ischemia, excessive calcium may be released leading to an activated state of OxPhos complexes including CcO. However, since oxygen, the substrate of CcO, is absent, the OxPhos process cannot proceed. During reperfusion in the presence of oxygen, maximal electron transfer rates occur due to hyperactivated OxPhos, followed by sharply increased mitochondrial membrane potential levels at which excessive ROS production occurs. High ROS levels may overwhelm endogenous antioxidant enzymes and cause irreparable damage to the cell. Thus, ROS play a role in ischemia-reperfusion injury.

In normoxia, CcO activity is down-regulated via phosphorylation. During ischemia, CcO becomes differentially phosphorylated or dephosphorylated but cannot operate due to the lack of oxygen. At the onset of reperfusion and in the presence of oxygen, the electron transport chain proton pumps operate at maximal activity, creating high mitochondrial membrane potentials, leading to the production of excessive ROS. Transient inhibition of CcO with infrared light avoids counteracts increased mitochondrial membrane potential levels and the production of ROS, and thus avoids counteracts cell death during reperfusion.

Figure 2A:
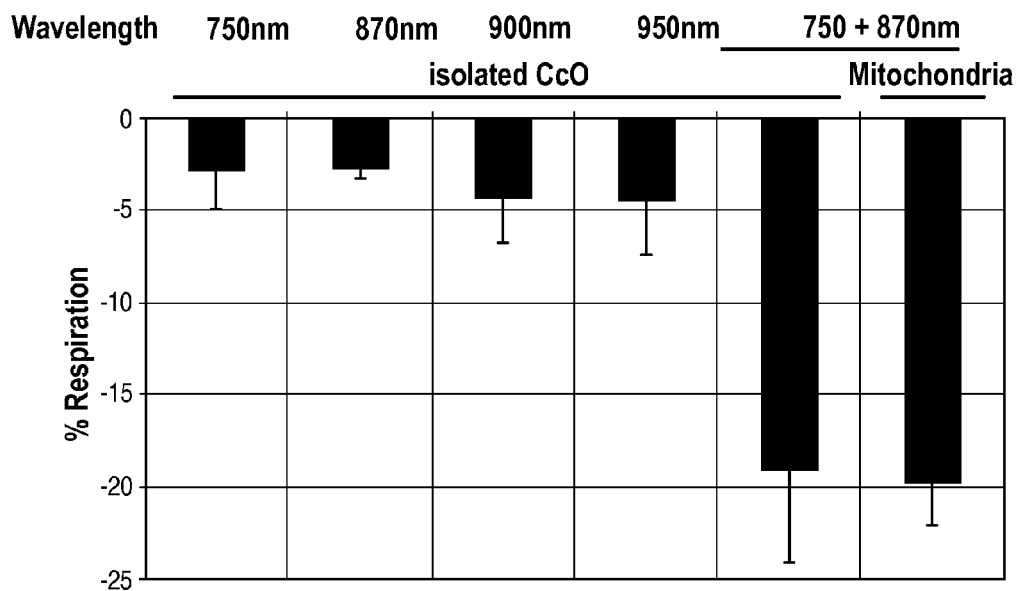
FIG. 2A illustrates an exemplary graph showing the effects of four exemplary wavelengths of infrared light emitted by low power diodes on isolated CcO and mitochondria.
Figure 2B:
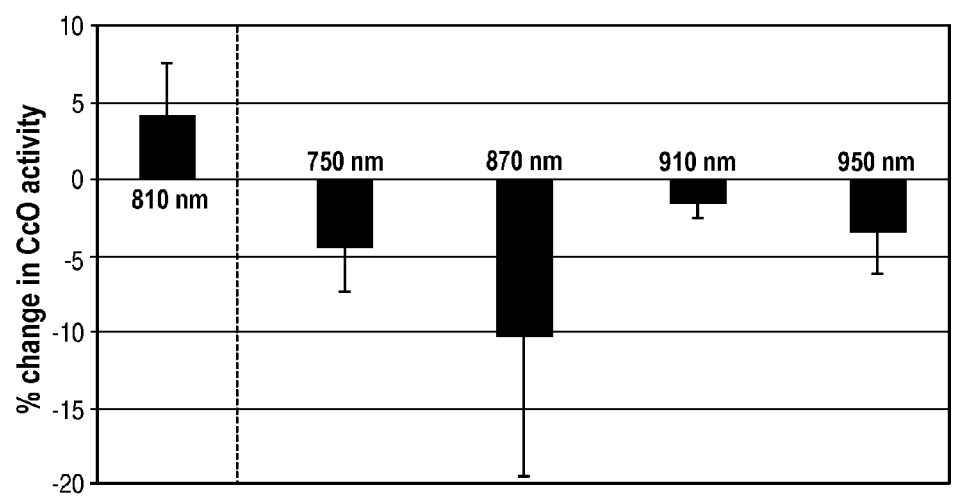
FIG. 2B illustrates an exemplary graph showing the effects of five exemplary wavelengths of infrared light emitted by high power diodes on CcO.

FIGS. 2A and 2B are graphs illustrating the effects of various wavelengths of infrared light emitted by low power diodes (FIG. 2A) and high power diodes (FIG. 2B) on CcO activity. Light with a wavelength within the ranges of approximately 730-770 nm, 850-890 nm, 880-920 nm, or 930-970 nm directly or indirectly inhibits CcO. FIG. 2A illustrates the effects that wavelengths of approximately 750 nm, 870 nm, 900 nm, and 950 nm have on CcO activity. However, any frequency within the ranges previously mentioned has a similar effect on CcO activity. Thus, any wavelength specifically mentioned herein is intended to include a range of wavelengths at least +/−20 nm from the specific wavelength disclosed. For instance, FIG. 2B illustrates that a wavelength of 910 nm has a similar effect on CcO activity as a wavelength of 900 nm.

Further, although the above exemplary ranges of approximately 730-770 nm, 850-890 nm, 880-920 nm, or 930-970 nm are disclosed, it is contemplated that such ranges are disclosed in the context of actual and known diode behavior. In one example, a diode outputs a radiant intensity that is approximately Gaussian in nature and centered approximately on a respective disclosed range. However, the range is determined in this example at approximately a mean radiant intensity level that, for a peak that is normalized to 1.0, falls at approximately 0.5 (or 50%) of the relative radiant peak. For instance, in the example of an 870 nm diode, the disclosed range of 850-890 nm is a range represented at approximately 50% intensity of the peak. Wings of the Gaussian distribution may extend outside the disclosed range for this exemplary diode, but at an intensity that is sub-50%. Thus, for the sake of disclosure and as described herein, although specific ranges for diode wavelengths are disclosed, it is contemplated that such diodes may equivalently include wavelengths that extend outside the disclosed range, albeit at intensity levels that may not be as clinically relevant, and having approximately a Gaussian distribution that is centered approximately in the center of the corresponding disclosed range of wavelengths.

Additional frequencies that inhibit CcO may be identified by integrating a customized light-protected oxygen electrode chamber with infrared light-permeable quartz windows into a double beam spectrophotometer and scanning the near infrared light ranges from, for instance 700 nm to 1000 nm and simultaneously recording changes in CcO activity using a polarographic method. The wavelengths identified in FIG. 2A to directly or indirectly inhibit CcO activity include 750 nm, 870 nm, 900 nm, and 950 nm. In addition, FIG. 2A illustrates a synergistic effect where dual wavelengths reduced respiration in both isolated CcO and mitochondria. Of course, as previously discussed, other wavelengths, taken alone or in combination, of infrared light may inhibit CcO besides those listed herein and shown in FIGS. 2A and 2B. Moreover, the wavelengths described herein are merely exemplary and may represent a range of frequencies centered around the frequency disclosed. For example, the wavelengths disclosed herein may be peak or middle wavelengths that represent a spectrum or range of wavelengths that reduce the effects of reperfusion injury. Indeed, additional wavelengths identified to inhibit CcO may be found in one or more of the following exemplary wavelength ranges: 730-770 nm, 850-890 nm, 880-920 nm, or 930-970 nm. Furthermore, reducing reperfusion injury using light may be the result of a synergistic effect caused by the light source outputting a range or spectrum of wavelengths.

Not all wavelengths between 700 and 1000 nm inhibit CcO. For example, as illustrated in FIG. 2B, a light source outputting light with a wavelength of approximately 810 nm may activate CcO instead of inhibit CcO. Activating CcO would have the opposite effect than intended. Specifically, activating CcO could actually increase cell damage and cell death caused by, for instance, reperfusion injury. Therefore, a wavelength of 810 nm alone or in combination with one or more of the wavelengths in the ranges previously described that directly or indirectly inhibit CcO may not produce the same benefits as using only wavelengths of light that inhibit CcO. To the contrary, the wavelength of 810 nm may negate or reverse the effects of wavelengths that inhibit CcO when applied prior to and/or during reperfusion. For at least this reason, the present treatment disclosed herein is distinguished from any prior treatment that applies light with a wavelength of or about 810 nm to ischemic tissue.

To analyze the effect of infrared light on CcO, the enzyme may first be purified. CcO may be isolated from, for instance, cow tissues since large amounts (e.g., 300 g) may be required to obtain adequate yield of purified CcO. Isolation of heart- and liver/brain-type CcO using an optimized protocol may yield a regulatory-competent enzyme. The heart and liver/brain isozymes differ by the presence of three different isoform subunits: VIa, VIIa, and VIII. The catalytic subunits that contain the proposed infrared light photoacceptors, the heme and copper centers, are identical between the isozymes, which may explain why various wavelengths of infrared light are effective in both the heart and brain, as well as other tissues.

For each wavelength and combination of wavelengths, an energy-dose response curve can be established by varying the light output from 0-2 $W/cm^2$ and measuring CcO activity using the polarographic method. After reaching a certain energy threshold, the inhibitory effect of infrared light may become saturated. Additional dose-response curves maybe recorded in the presence of the allosteric activator ADP and the allosteric inhibitor ATP including an ATP-regenerating system. Infrared light may affect CcO in multiple ways. Thus, in addition to analyzing CcO kinetics, proton pumping efficiency may also be assessed.

Following transient global cerebral ischemia, there is a morphological progression of neuronal injury that occurs in specific populations of neurons that are highly susceptible to damage and death. Hippocampal CA1 neurons are particularly sensitive to an ischemic insult, and a near-complete loss is observed at three to seven days after reperfusion in a rat animal model. ROS may play a role in the pathophysiology of neuronal death. Therefore, the neuroprotective effect of infrared light are defined in terms of its ability to prevent degeneration of neurons in the CA1 hippocampus. For instance, using simulated brain ischemia in rats showed significant neuroprotection with infrared light treatment. Specifically, rats were exposed to eight minutes of global brain ischemia (bilateral carotid artery occlusion coupled with induced transient hypotension) with or without infrared light treatment for the final two minutes of ischemia and the first two hours of reperfusion using a device having a power output of approximately 200 $mW/cm^2$ and outputting light with wavelengths of approximately 750 nm, 870 nm, 900 nm, and 950 nm. This revealed significant neuroprotection with infrared light treatment (in this example rats treated with infrared light showed 66% protection, a greater than 10-fold increase in neuronal number versus the untreated group). Further, the above powers were applied in vivo and with rats. Accordingly, power output ranging from 500 $mW/cm^2$-5 $W/cm^2$ is contemplated in human treatments. For neonates and infants lower ranges toward 500 $mW/cm^2$ are contemplated, while for adults a range of 2-4 $W/cm^2$ or greater may be applicable.

Figure 3:
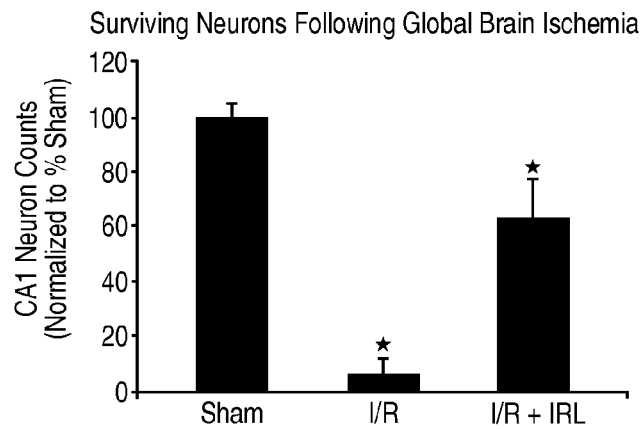
FIG. 3 is a graph illustrating exemplary neuron counts in the CA1 hippocampus of three groups of rats following testing treatments using low power diodes.
Figure 4:
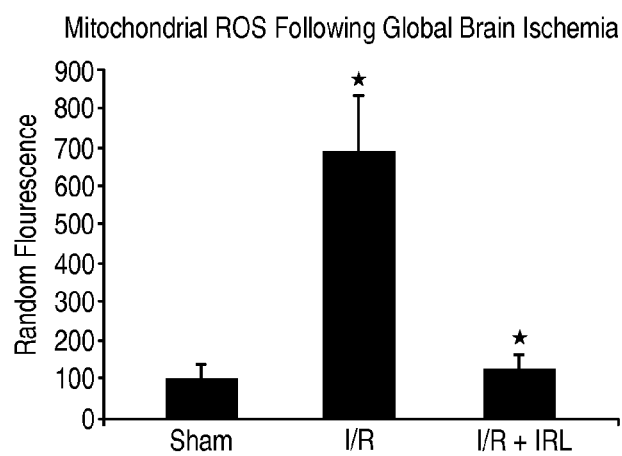
FIG. 4 is a graph of exemplary ROS including superoxide production illustrating relative fluorescence following global brain ischemia of the three groups of rats following use of lower power diodes.

FIGS. 3-7 are graphs that include various results of treatments performed on rats. Specifically, FIG. 3 illustrates the neuron counts in the CA1 hippocampus of a non-ischemic sham-operated animal (Sham), a rat that underwent eight minutes of global brain ischemia followed by seven days of reperfusion (I/R), and a rat that underwent eight minutes of ischemia followed by seven days of reperfusion while being treated with infrared light (I/R+IRL) (IRL designating the infrared light) generated by low power diodes. FIG. 4 is a graph of superoxide production illustrating the relative fluorescence of the Sham, I/R, and I/R+IRL groups of rats. The rats that underwent the infrared light treatment had higher neuron counts (FIG. 3) and lower levels of mitochondrial ROS (FIG. 4) than those rats that were simply subject to reperfusion following global brain ischemia.

Infrared light may further have a cardioprotective effect following myocardial ischemia/reperfusion. For instance, in one example, rats underwent 45 minutes of left coronary artery occlusion followed by two hours of reperfusion. In the infrared light-treated rats, irradiation of the anterior wall of the heart (e.g., the area perfused by the left coronary artery) was initiated during the final ten minutes of occlusion and was maintained throughout the two-hour reperfusion period using a device having a power output of approximately 200 $mW/cm^2$ and outputting light with at least wavelengths of about 750 nm, 870 nm, 900 nm, and 950 nm. Infarct size was delineated by triphenyltetrazolium chloride staining and expressed as a percent of the risk region (e.g., the extent of the ischemic myocardial bed). This revealed significant cardio protection with infrared light treatment (e.g., infarct size in the treated versus control groups averaged 20+/−5% of the myocardium at risk versus 59+/−5% of the myocardium at risk, respectively).

Figure 5:
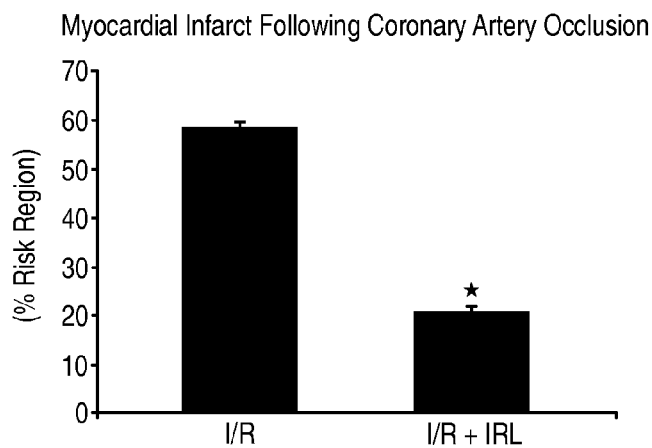
FIG. 5 illustrates myocardial infarct size of the I/R group of rats compared to a control group using low power diodes.
Figure 6:
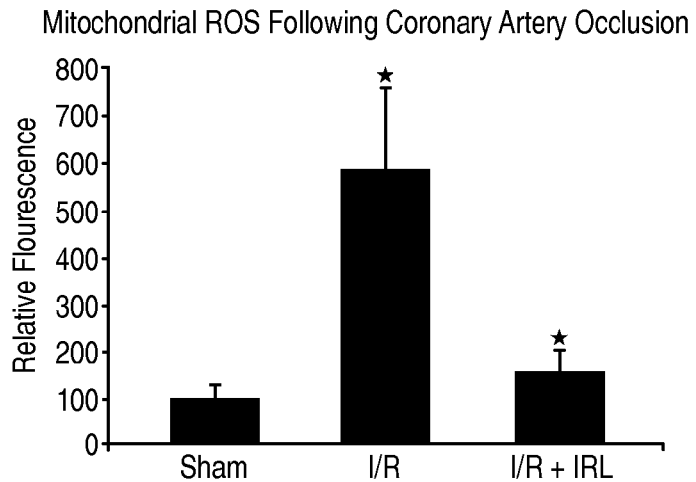
FIG. 6 is a graph illustrating relative fluorescence of exemplary ROS including superoxide production following coronary artery occlusion of three groups of rats using low power diodes.

FIG. 5 illustrates the myocardial infarct size of the rats in the I/R group, versus the control group following coronary artery occlusion. FIG. 6 is a graph illustrating relative fluorescence of exemplary ROS including superoxide production following coronary artery occlusion of the three groups of rats. FIGS. 5 and 6 illustrate the benefits to rats that received the light treatment compared to rats that did not.

Figure 7:
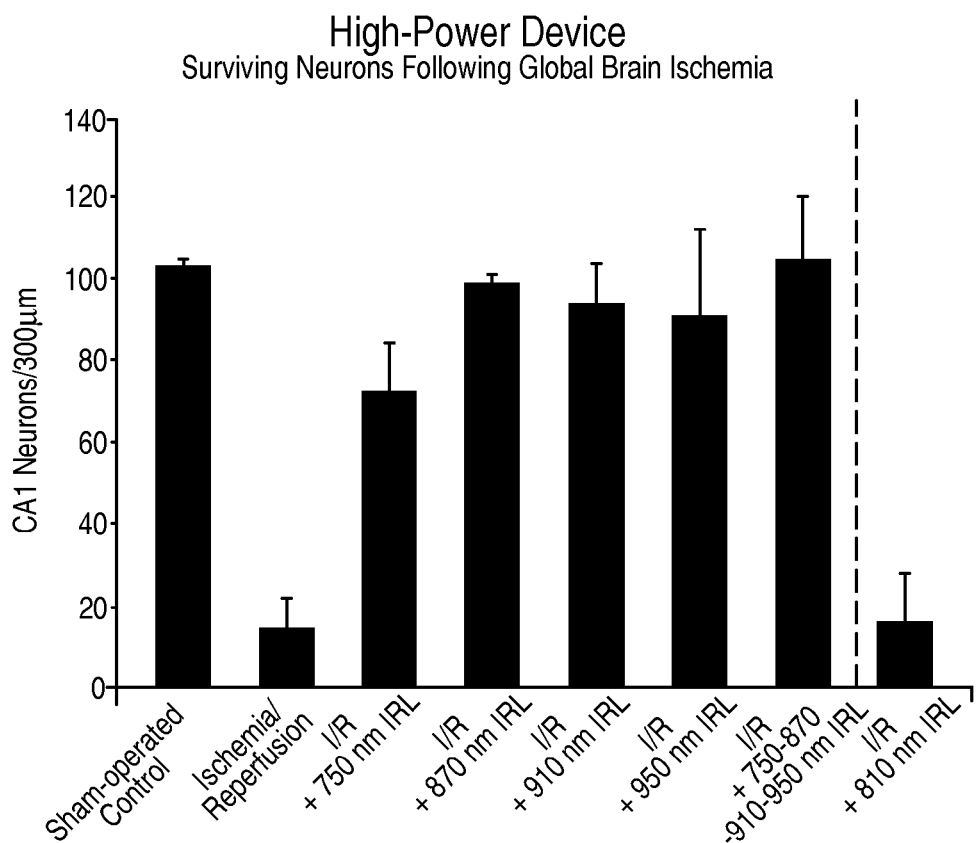
FIG. 7 is a graph illustrating exemplary neuron counts in the CA1 hippocampus of various groups of rats following treatments for global brain ischemia using high power diodes.

Using high power diodes generates similar results. For example, FIG. 7 is a graph illustrating exemplary neuron counts in the CA1 hippocampus of the various groups of rats following a light treatment for global brain ischemia using high power diodes. As illustrated, the rats that received the light treatment described herein had higher neuron counts following global brain ischemia than those that did not. Therefore, both low power diodes and high power diodes provide beneficial effects when used with the treatment disclosed herein. Further, as illustrated, a wavelength of 810 nm does not result in improved neuron survival.

Figure 8:
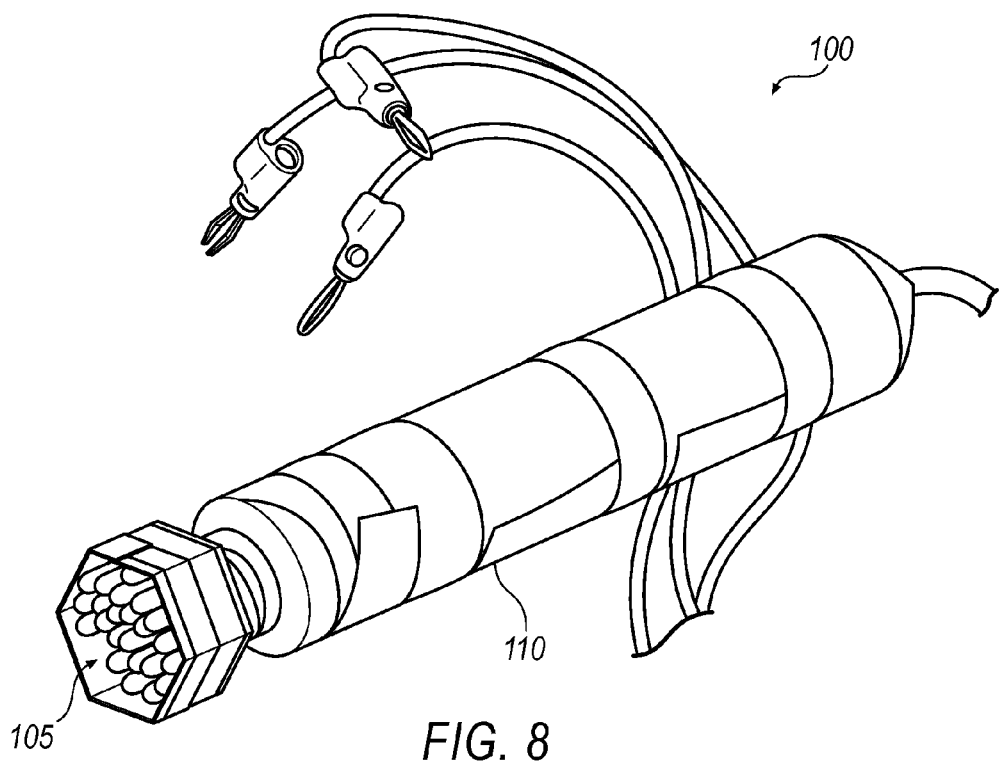
FIG. 8 illustrates an exemplary light therapy device to inhibit CcO and reduce reperfusion injury.

FIG. 8 illustrates an exemplary light therapy device 100 that may be used to directly or indirectly inhibit CcO using infrared light, and thus reduce reperfusion injury. The light therapy device 100 includes at least one light source 105 configured to output light at a wavelength that inhibits CcO when the light is applied to an ischemic area of tissue before, during, and/or after reoxygenation or clinical intervention. The light source 105 may include a light emitting diode (LED), a laser diode, optical fibers, or any other source that is configured to emit light with a wavelength that, for instance, directly or indirectly inhibits CcO when applied prior to reperfusion, and when applied during reperfusion as well. For instance, the light source 105 may include any light source 105 that is configured to output light with a wavelength of 750 nm, 870 nm, 900 nm, or 950 nm. Other light sources 105 may include quadruple diodes or a combination of individual wavelength diodes. Further, the light sources 105 may be high power or low power. The type of light source 105 may depend upon the application. For instance, optical fibers may be used to deliver light to areas of the body that may be difficult to reach with larger light sources and thus provide infrared treatment through the mouth, ears, nose, etc. In one example, diodes may be cooled during use, and before the next use, to avoid localized tissue heating that could have adverse consequences.

The light therapy device 100 may include any number of light sources 105, for instance, arranged in an array such as a diode array or a fiber optic array. Each of the light sources 105 in the array may output light with one of the wavelengths that inhibit CcO. In one exemplary implementation, some of the light sources 105 in the array may output light with one wavelength while other light sources 105 in the array may output light with a different wavelength. Therefore, the light sources 105 in combination may output light having multiple wavelengths that inhibit CcO and reduce reperfusion injury.

Moreover, the light sources 105 are configured to output light with a power density that is sufficient to at least partially penetrate one or more body tissues such as skin, bone, muscle tissue, and organs. In one exemplary approach, each light source 105 is configured to output light with a power density of at least approximately 200 mW/cm$^2$. For instance, each light source 105 is configured to output light with a power density of at least approximately 800 mW/cm$^2$ when used with an adult human, and up to 5 W/cm$^2$ in some applications. Alternatively, in another example, if the light therapy device 100 is used with, for example, a neonate (i.e., a newborn of approximately four weeks or less), the power density may be lower. One or more of the light sources 105 in the array may have a different power density than one or more of the other light sources 105 in the array. Further, the power density of each light source 105 is related to the wavelength of light generated by the light source 105. Therefore, light sources 105 generating light with the same wavelength are output with the same power density while light sources 105 generating light at different wavelengths may be output with different power densities. However, it is contemplated that the light sources in this and all disclosed exemplary embodiments may range in power output density up to 5 W/cm$^2$.

The light therapy device 100 further includes a portion, such as a handle 110, that houses various electronics that allow the light sources 105 to operate correctly. For instance, the handle 110 may include one or more processors and circuit boards that control operation of the light sources 105, including enabling and disabling the light sources 105, adjusting the brightness of the light sources 105, etc. Alternatively, some of the electronics used to operate the light sources 105 may be housed in a separate device other than the light therapy device 100.

The light therapy device 100 illustrated is merely exemplary and may take other forms. For instance, the light therapy device may be incorporated into a helmet for brain treatments, a catheter for combined clot removal and infrared light treatment, a mouthpiece or toothbrush to treat dental/gum disorders, a massage device, diabetic socks or slippers, a headband to treat headaches, an eye mask to treat eye diseases, a glove to treat gout or arthritis, a laser pointer to treat locally (e.g., a cold sore), a cushion, a blanket, a belt, a foot bath, a belly belt to help, for example, women at risk for preterm birth, a back belt to treat back pain, or an infrared pill charged via induction to treat intestinal diseases, a tanning booth for cosmetic purposes (e.g., wrinkle reduction), etc. The light therapy device 100 may be further configured to perform other tasks than described. For instance, the light therapy device 100 may be configured to act as an oximeter and monitor oxygen. Alternatively, the light therapy device 100 may be configured to work with one or more oximeters. If so, the light therapy device 100 may include a controller that prevents light used during treatment from interfering with light used to measure oxygen saturation.

Figure 9:
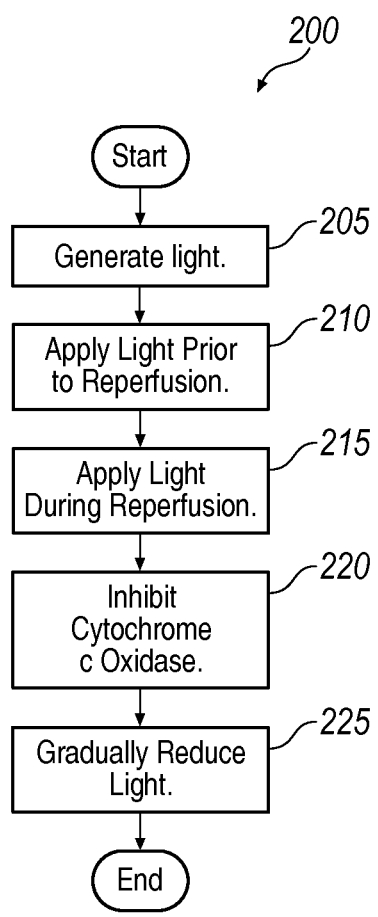
FIG. 9 illustrates an exemplary flowchart of a process to reduce the risk of reperfusion injury following an ischemic event.

FIG. 9 illustrates an exemplary flowchart of a process 200 that may be used to reduce the risk of reperfusion injury following an ischemic event. Block 205 includes generating light using, for instance, one or more light sources 105. The light source 105 may include a light emitting diode (LED), an optical fiber, a laser, or any other light source 105 configured to output light having a wavelength that directly or indirectly inhibits CcO. Furthermore, the light source 105 is configured to output light with a range that includes multiple wavelengths. One or more of the wavelengths in the range may inhibit CcO to reduce reperfusion injury when applied before, during, and/or after reoxygenation of ischemic tissue. For instance, the light source 105 may output light with a wavelength of approximately 750 nm, 870 nm, 900 nm, or 950 nm. Additionally, the light source 105 may output light at one or more of these wavelengths, as well as other wavelengths that inhibit CcO. Moreover, the light source 105 is configured to output light having a power density sufficient to penetrate one or more body tissues. For instance, the power density may be sufficient to penetrate one or more of bone, skin, muscle tissue, and organ tissue. In one exemplary approach, the light source 105 may generate the light with a power density of at least approximately 200 mW/cm$^2$. For example, the light source 105 may generate the light with a power density of at least approximately 800 mW/cm$^2$ when used on an adult human or less than 200 mW/cm$^2$ when used on, for instance, neonates.

Block 210 includes applying light to an ischemic area of tissue prior to reoxygenation of the tissue, such as before or during clinical intervention. As previously discussed, various wavelengths of infrared light, alone or in combination, inhibit CcO when applied, for example, no later than the onset of reperfusion and at least partially during reperfusion, reducing the effects of reperfusion injury. In one exemplary approach, using the exemplary light therapy device 100 illustrated in FIG. 7, a physician may direct the light generated by the light source 105 toward the ischemic area of a patient's body prior to, or after the onset of reperfusion or prior to, or after initiating a clinical intervention. A clinical intervention may include, for example, administering a clot-busting drug, inflating/deflating an angioplasty balloon, resuscitation, transfusion, or administering vasoactive drugs, among others. As previously discussed, reperfusion is defined as the process where oxygen and other nutrients are restored to ischemic tissue. The onset of reperfusion is defined as the instant in which reperfusion begins. Prior to the onset of reperfusion, the physician may direct the light onto the patient's skin, and the light may pass through the patient's skin, bone, muscle tissue, organs, or any other tissue prior to reaching the ischemic area. In all examples disclosed herein, even if treatment is delayed and not applied prior to the onset of reperfusion, it is understood that subsequent treatment nevertheless provides the disclosed benefits despite the delay, although delayed treatment may reduce the degree of benefit accrued. The physician may apply glycerol to the patient's skin to help the light penetrate the patient's skin. Glycerol helps make the skin transparent to infrared light. Alternatively, before reperfusion, the physician may direct the light directly onto the ischemic area if the ischemic area is exposed (e.g., via a surgical opening).

Block 215 includes applying the light at least partially during reoxygenation. In addition to applying the light prior to reoxygenation as illustrated at block 210, applying the light to the tissue at least partially during reperfusion may further inhibit CcO and further reduce the effects of, for instance, reperfusion injury. Much cellular damage occurs at the onset of or during reperfusion due to hyperactive OxPhos enzymes. Accordingly, applying the light at the onset of reperfusion and continuing to apply the light for some amount of time during reperfusion may further directly or indirectly inhibit CcO and reduce cell death and damage. In some instances (e.g., brain ischemia), applying the light shortly after reperfusion begins may still reduce cell death and damage, but to a lesser degree than if the light were applied prior to the onset of reperfusion. In one exemplary implementation, the light may be applied until reperfusion is complete, or alternatively, the light may be applied for a predetermined amount of time relative to when reoxygenation began. For instance, the physician may continue to apply the light for two hours following the onset of reperfusion.

Block 220 includes inhibiting CcO using the light from the light therapy device 100. As previously discussed, applying light at various frequencies to ischemic tissue prior to and at least partially during reoxygenation or clinical intervention directly or indirectly inhibits CcO. Inhibiting CcO indirectly prevents the generation of free radicals that may trigger cellular death and damage in the affected tissues. As previously discussed, cytochrome c and the CcO enzyme include photoacceptors that receive the light generated by the light therapy device 100. When the light output by the light therapy device 100 penetrates the various body tissues and reaches the ischemic area, the light inhibits CcO and thus reduces cell damage caused by ischemia/reperfusion injury.

Block 225 includes gradually reducing the light to the treated tissue. For instance, the light output by the light therapy device 100 may be gradually reduced following the onset of reperfusion or after reperfusion is complete. In one exemplary approach, the physician may manually reduce the light output of the light therapy device 100 by disabling one or more of the light sources 105 in the array or by moving the light therapy device 100 further away from the patient. Alternatively, the light therapy device 100 may be configured to gradually reduce the brightness of one or more of the light sources 105 or disable the light sources 105 one at a time or in discrete groups so that the light applied to the ischemic area is automatically reduced.

Figure 10:
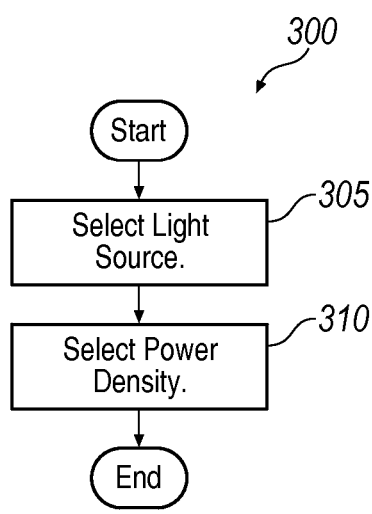
FIG. 10 illustrates an exemplary flowchart of a process that may be used to design a device configured to inhibit CcO, such as the exemplary light therapy device illustrated in FIG. 8.

FIG. 10 illustrates an exemplary flowchart of a process 300 that may be used to design a device configured to inhibit CcO, such as the light therapy device 100 illustrated in FIG. 8.

Block 305 includes selecting at least one light source 105. The light source 105 is configured to generate light having a wavelength that, for example, inhibits CcO during reoxygenation of ischemic tissue. The selected light source 105 may generate light having a wavelength that includes one or more of approximately 750 nm, 870 nm, 900 nm, and 950 nm. Selecting the light source 105 may further include arranging a plurality of light sources 105 in an array. In this exemplary approach, each of the light sources 105 may have a wavelength that inhibits CcO during reoxygenation of ischemic tissue. Some light sources 105 in the array may be selected to include different wavelengths than other light sources 105 in the array. For instance, some of the light sources 105 may output light with a wavelength of about 750 nm, some of the light sources 105 may output light with a wavelength of about 870 nm, some of the light sources 105 may output light with a wavelength of about 900 nm, and some of the light sources 105 may output light with a wavelength of about 950 nm. Of course, other wavelengths of light may inhibit CcO and may be used in the array. Also, the array need not include equal numbers of each type of light source 105.

Block 310 includes selecting a power density of the light source 105 sufficient for the light generated by the light source 105 to penetrate a body tissue. If the light sources 105 are arranged in an array, one or more of the light sources 105 may output light with a different power density than another of the light sources 105. The power density may further depend upon how the light is applied by the physician. For instance, if the physician applies the light to the patient through the patient's skin, bone, muscle tissue, and organs, then a higher power density may be necessary than if the light is applied directly to the ischemic tissue through, for instance, a surgical opening.

Another consideration when selecting power density may include reducing the amount of thermal damage to the patient. For instance, the power density may be selected so that the tissue to which the treatment is applied does not heat by more than one degree Celsius during the treatment. In one exemplary approach, the power density may, for instance, be at least approximately 200 mW/cm$^2$. In another exemplary approach, for instance in an adult human patient, the power density may be at least approximately 800 mW/cm$^2$. However, the power density may be lower than 200 mW/cm$^2$ when used with other human patients, such as neonates.

The treatment previously described may have various applications. For instance, the treatment may be used to treat any tissue damage resulting from increased ROS and/or conditions where reduction of cellular energy is favorable. As previously discussed, the apparatus and methods described herein may reduce the effects of ischemia and reperfusion injury (e.g., heart attack and stroke). In addition, the apparatus and methods may be beneficial during organ transplantation, during any surgery that involves transient interruption from blood supply such as a bypass surgery and other heart surgeries, when treating trauma including brain and spinal cord trauma, during wound healing such as in patients with diabetes, when treating neonatal brain hypoxia/ischemia or acute tubular necrosis, during cosmetic procedures (e.g., wrinkle reduction), during preterm birth, and during prenatal and/or postnatal care (e.g., necrotizing enterocolitis), when treating pain such as back pain, etc.

The apparatus and methods described herein may further be used to treat a variety of pathological conditions, to include muscle spasms, asthma, epilepsy, erectile dysfunction, insomnia, abdominal and cerebral aneurysms, or inflammation and other diseases with increased ROS including eye diseases such as uveitis, diabetic retinopathy, or cataracts, gum inflammation, arthritis, atherosclerosis, burns, viral infections such as cold sores or herpes, balding or gray hair, allergies, autoimmune disorders (e.g., systemic lupus), dermatitis, Crohn's disease, dicubity (e.g., bedsores), etc. The present disclosure may further address other pathological conditions by reducing neurodegeneration such as that caused by Alzheimer's disease, Parkinson's disease, multiple sclerosis, or amyotrophic lateral sclerosis (ALS). The treatment described herein may have additional uses besides those explicitly disclosed, including additional uses in human and/or veterinary medicine. Thus, for the purposes of this disclosure, the terms "pathology" and "pathological condition(s)" broadly refer to at least any of the above described conditions that may be treated using IRL treatment as disclosed herein.

Figure 11:
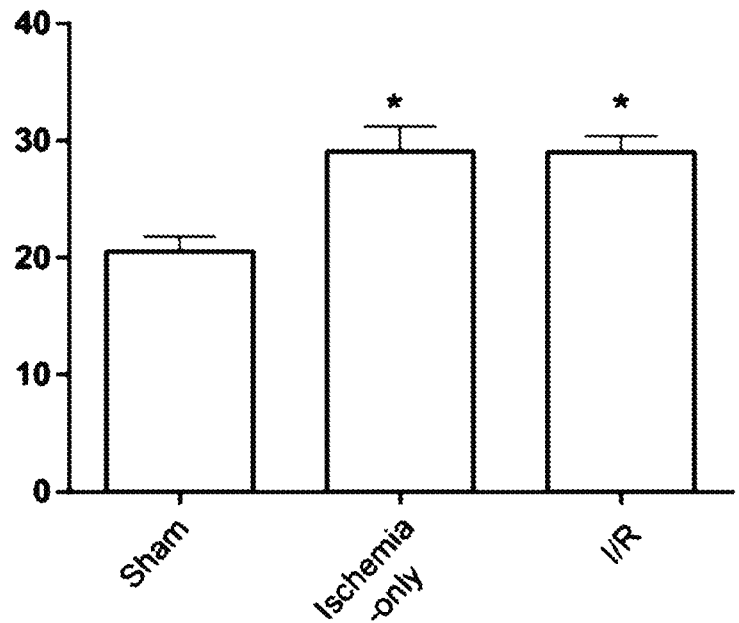
FIG. 11 illustrates CcO specific activity showing hyperactivation after ischemia and during reperfusion following ischemia (I/R) in comparison to controls (sham).

According to the above, four wavelengths of infrared light (IRL) have been identified that directly affect CcO and reduce CcO activity. The underlying mechanism for the disclosed benefits is that there is an increased CcO activity that occurs during ischemia and during reperfusion. That is, referring to FIG. 11, CcO activities are illustrated of ischemia-only and ischemia/reperfusion (I/R) compared to controls (sham), showing that the enzyme is hyperactive in the relative scale of the illustrated CcO activity after ischemia and during reperfusion following ischemia (I/R).

Neonatal Hypoxia/Ischemia

Impaired cognitive and neuromuscular development in infants and children can result from in utero and intrapartum cerebral insults. While a number of factors ranging from prematurity to maternal infection can contribute to aberrant neural development, cerebral oxygen deprivation is a well-established cause of damage. The occurrence of asphyxial events among hospital deliveries is ~2-4 per 1000 full-term births. Preterm birth can often be associated with in utero hypoxia or compromised cerebral oxygen levels during delivery, thus leading to a high incidence and severity of hypoxic/ischemic encephalopathy (HIE) among premature neonates. HIE has been associated with severe cerebral injury leaving the infant at risk for motor disorders, delayed mental development, coordination problems, and vision and hearing impairments. Compromised oxygen delivery in utero results in more subtle damage, with symptoms manifesting during early childhood. Given the varied causes and severities of HIE, it is desired to have a therapy that can be safely administered to infants (premature or at term) when oxygen compromise is suspected. Therapeutic IRL treatment will provide a safe method to treat damaging processes in the brain on any newborn with evidence of fetal distress, without concerns of compromising undamaged tissues.

Timely restoration of blood flow and/or oxygen delivery to the brain is important in order to salvage ischemic neurons. However, it is well-recognized that reperfusion or reoxygenation per se precipitates additional, significant components of irreversible tissue damage, attributed in large part to reintroduction of oxygen and the resultant generation of ROS. The resulting spectrum of injury, termed neonatal HIE can result in extensive brain damage and a myriad of early childhood developmental delays or neurocognitive deficits. Infrared light presents a novel non-invasive therapeutic strategy to target reperfusion injury. This technology is based on: (i) the discovery that specific wavelengths of infrared light (IRL) modulate the activity of mitochondria by reducing CcO activity and, as a result attenuate ROS generation; and (ii) data presented here demonstrating that application of IRL at the onset of reperfusion, or after a delay of treatment is effective, which is profoundly neuroprotective in the neonatal brain.

Much of the research aimed at controlling ROS damage in stroke and heart attack has focused on pharmacologic scavenging techniques. This approach has yielded inconsistent results in experimental models and did not translate into clinical therapies. This is likely due to the inherent difficulties in delivering adequate drug concentrations to the appropriate subcellular sites within the important early seconds-minutes of reflow. The disclosed non-invasive approach, reducing the production of ROS (rather than scavenging ROS) can circumvent this intrinsic barrier to the treatment of reperfusion injury by allowing direct irradiation from the outside of the scalp.

To optimize the neuroprotective effect of IRL irradiation in the neonatal brain, wavelengths are identified that are most effective in evoking neuroprotection therein. Two wavelengths that show maximum and statistically equivalent neuroprotection are 750 nm and 950 nm. Accordingly, these wavelengths have been tested in a Vannucci rat model of neonatal hypoxia/ischemia.

In one experiment, seven-day-old Sprague-Dawley rats (body weight: 17±0.6 g) were subjected to carotid artery ligation under isoflurane anesthesia. After ligation, the pups were returned to their dams and allowed to recover for 2 hours. To induce hypoxia, pups were placed into a temperature-controlled chamber and exposed to 8% oxygen/92% nitrogen for 120 min at 37° C. Following hypoxia, all animals were randomized to an IRL-treated or control group and immobilized under a fiber optic light guide that delivered therapeutic IRL. A fiber-optic light guide was placed directly above the dorsal scalp surface, and diodes were located at a distal end, 30 cm (or approximately 12 inches) away from the pup. For animals randomized to IRL treatment, the head was irradiated for 1 hour at a fluence of 50 $mW/cm^2$. All animals were maintained normothermic during treatment including non-IRL-treated controls. Untreated controls were positioned on the same homeothermic warming blanket, with a light guide that had no light administered.

Twenty-four hours post-hypoxia, brains were sectioned at a uniform thickness (1 mm) with a vibratome (in this example, a Campden Instruments MZ5000 was used) and incubated in triphenyltetrazolium chloride (TTC) warmed to 37° C. for 15 min. Using this method, viable tissue stains red while necrotic tissue remains unstained. Brain slices were imaged and infarct volume was calculated as a ratio of the hemisphere volume on the contralateral side to compensate for brain edema.

Figure 12:
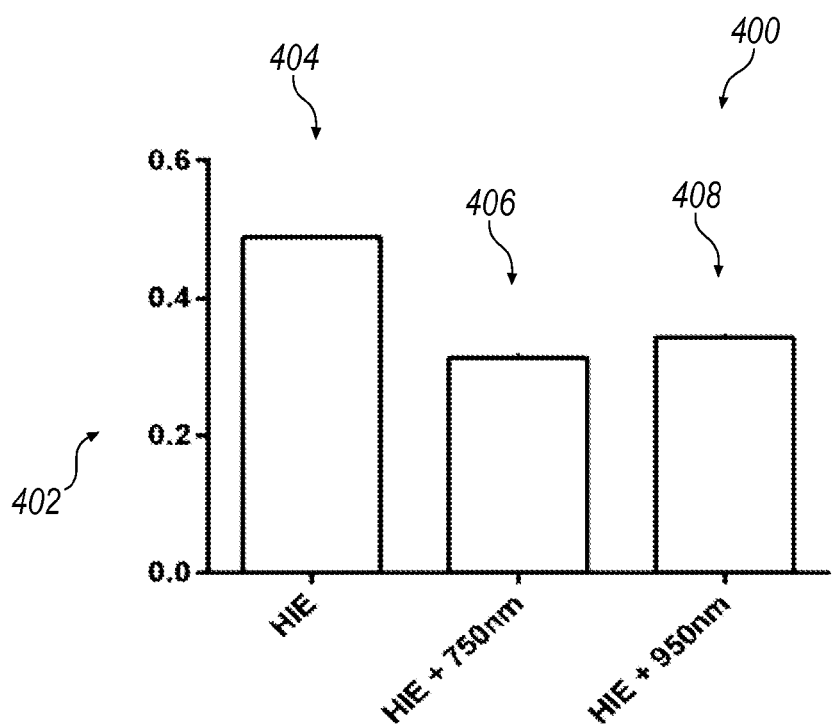
FIG. 12 is a graph showing a fraction that illustrates an exemplary amount of infarction observed in an exemplary dataset in a neonatal hypoxia/ischemia study for HIE, HIE+ 750 mm and HIE+950 nm.

Accordingly, FIG. 12 illustrates a graph 400 showing a fraction 402 that illustrates an amount of infarction observed in an exemplary dataset. In this illustrated example, HIE 404 showed approximately 0.5, or 50% infarct. However, for HIE and 750 nm treatment as described 406, the fraction of infarct reduced by approximately 0.3, or 30%, and for HIE and 950 nm treatment 408, the fraction of infarct reduced by approximately 0.33, or 33%. For groups of 16, results demonstrate a significant neuroprotective effect of 750 nm and 950 nm IRL treatment. Groups were compared using a one-way ANOVA followed by a Tukey's HSD test for post hoc analysis to statistically evaluate differences between groups. These data demonstrate that IRL administration provides cerebral protection to the neonatal brain following hypoxic insults.

Multiple Sclerosis

Multiple sclerosis (MS) is a known autoimmune disorder. It is a chronic inflammatory disease that leads to demyelination of the nerve cells in both the brain and the spinal cord, i.e., the nerve cells lose their insulation. Several phases in the course of the disease have been defined including relapsing MS, in which the symptoms occur in isolated attacks, or progressive MS, in which symptoms become worse over time.

In the experiments described below, a mouse model of MS was treated daily with 950 nm infrared light for two weeks to observe the effect of this treatment on the clinical, histological and cell biological outcome of this disease. In this way it is demonstrated that daily infrared light treatment ameliorates the neurological symptoms and cell biological response in this mouse model. Infrared light of 950 nm could thus be a useful adjunct treatment for patients with MS.

The mouse model of MS used in these experiments is called a MOG (myelin oligodendrocyte glycoprotein) peptide model of EAE (experimental autoimmune encephalomyelitis). Myelin is a membrane insulation surrounding axons in the central nervous system (CNS) and acts to facilitate the conduction of nerve impulses. Myelin is produced by oligodendrocytes, one of the several so-called glial cells in the brain. Myelin is composed mainly of lipids (that is, fat) but also contains a number of proteins specific to myelin, one of which is MOG. Immunization of a mouse with MOG, or pieces of MOG such as the MOG peptide, produces an immune response to myelin similar to that seen in patients with MS. After the injection of MOG the mice present with clinical signs and symptoms of neurological dysfunction, mainly limb weakness, similar as seen in patients with MS, and injury to myelin and nerve cells can be found in their brains.

To produce this animal model, a small piece of the MOG protein containing amino acids 35-56 is injected into the abdominal cavity of adult C57BL/6 mice along with Freund's complete adjuvant and pertussis toxin. The disease caused by this response, EAE, characterized by hind limb weakness, usually begins after a 10 to 14 day latent period. During this asymptomatic period, white blood cells specific for attacking MOG are produced first in the blood and then traffic to the brain and spinal cord. Consistent with the symptoms of EAE, examination of brain and spinal cord tissue from these mice at the time-point at which weakness first appears demonstrates that white cells have invaded the white matter portion of the brain and have damaged both myelin and axons. Interestingly, these EAE brain lesions resemble one of the classic patterns of tissue injury seen in multiple sclerosis plaques, suggesting that MOG EAE is an adequate model of this disease.

Infrared light therapy attenuates the clinical course of MOG-induced EAE. Female C57BL/6 mice, 6-8 weeks old were immunized with myelin oligodendrocyte glycoprotein (MOG) peptide 35-55, MEVGWYRSPFSRVVHLYRNGK emulsified with complete Freund's adjuvant (CFA) containing heat inactivated Mycobacterium tuberculosis by subcutaneous injection. Control animals were immunized with an equivalent volume of CFA emulsion that did not contain MOG peptide. Mice were also immunized by intra-peritoneal (ip) injection with pertussis toxin immediately after MOG immunization and 2 days later. Mice were evaluated on a daily basis for changes in body weight, overt signs of illness, and clinical signs of EAE using a 5-point scoring system: 0—no symptoms; 1—limp tail; 2—limp tail and gait imbalance or hind limb weakness; 3—partial hind limb paralysis; 4—full hind limb paralysis; 5—moribund state or death.

Figure 13:
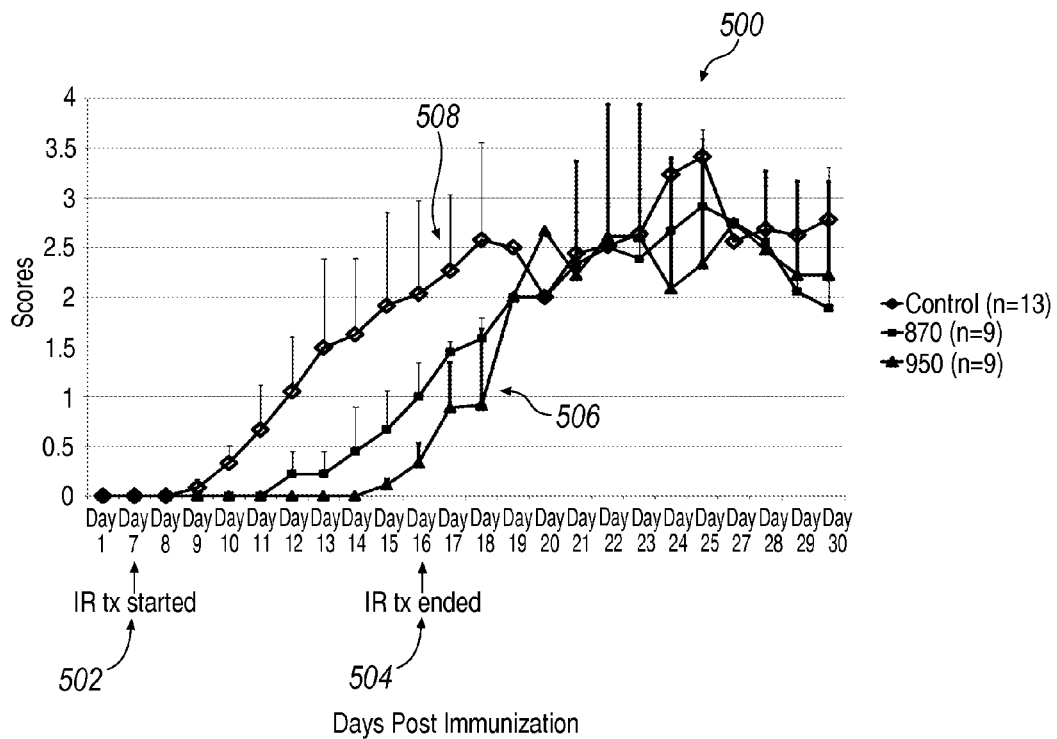
FIG. 13 is a graph showing mouse response for IRL treatment in a multiple sclerosis (MS) animal model study using 870 nm and 950 nm.

Referring to FIG. 13, graph 500 shows infrared light treatment at 870 nm and 950 nm applied to separate groups of mice, at a distance of 2 cm from the head/spinal cord with a diode power output of 200 mW/cm$^2$, was started 502 (on day 7) 7 days after the immunization for 2 hours/day for 10 days 504. The head and back areas of the animals were shaved one day before the treatment to increase the efficiency of the IRL penetration, and the skin was wiped with glycerol just before each treatment session since it makes the skin transparent to IRL. The animals were restrained in a plastic cylinder with an open top covered with a wire grid to expose the spinal and cranial area to the light. The control EAE animals were treated similar to the IRL-treated group but the IRL was not turned on. As can be seen, irradiation of mice with either of these two wavelengths attenuated 506 the clinical course of EAE when compared to the control 508. The treatment effect, however, did not persist after irradiation was stopped.

Infrared light therapy reduces the number of fluorogenically dyed positive spleen cells. Spleens from both treated and untreated MOG-induced EAE mice were removed and minced in PBS (phosphate buffered saline) with 2% FBS (fetal bovine serum) and passed through a 70 micron cell mesh filter. Following the red blood cell lysis, a single cell suspension was cultured in complete DMEM medium and then stained with a red fluorogenic dye at 37° C. for 15 minutes. The number of stained cells were measured by flow cytometry. The cells in this culture are predominantly white blood cells since they came from the spleen where these cells are known to accumulate. The number of cells showing fluorescence is a measure of how many cells are producing reactive oxygen species (ROS) in the mitochondria, chemical compounds implicated in the tissue damage both in EAE and in MS.

Figure 14:
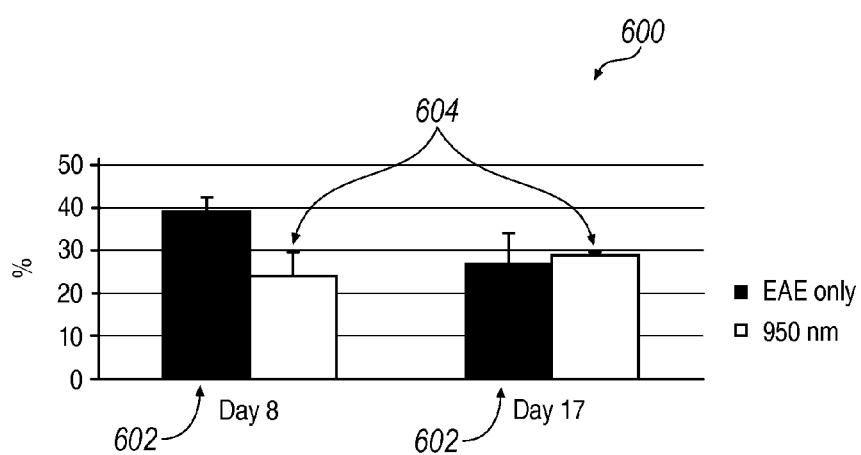
FIG. 14 is a chart with percentage of MitoSox positive spleen cells for EAE only and for 950 nm treatment after EAE induction in a multiple sclerosis (MS) animal model study.

Referring to FIG. 14, chart 600 shows percentage of MitoSox positive spleen cells for EAE only 602 and for 950 nm treatment 604 for both 8 and 17 days after EAE induction. As seen, there are significantly fewer MitoSox positive spleen cells observed in the IRL-treated animals one day after initiation of irradiation (i.e., 8 days after EAE induction), although both treated and untreated animals had a similar number of MitoSox positive cells after 10 days of infrared irradiation (i.e., 17 days after EAE induction). These data suggest that the effect of IRL on the course of EAE is due, at least in part, to the reduction of mitochondrial ROS production by activated lymphocytes in the blood.

The effect of infrared light therapy on EAE persists during prolonged treatment. As previously discussed, infrared light ameliorates the clinical course of EAE between days 8 and 17, but that the effect did not persist after treatment was terminated.

Figure 15:
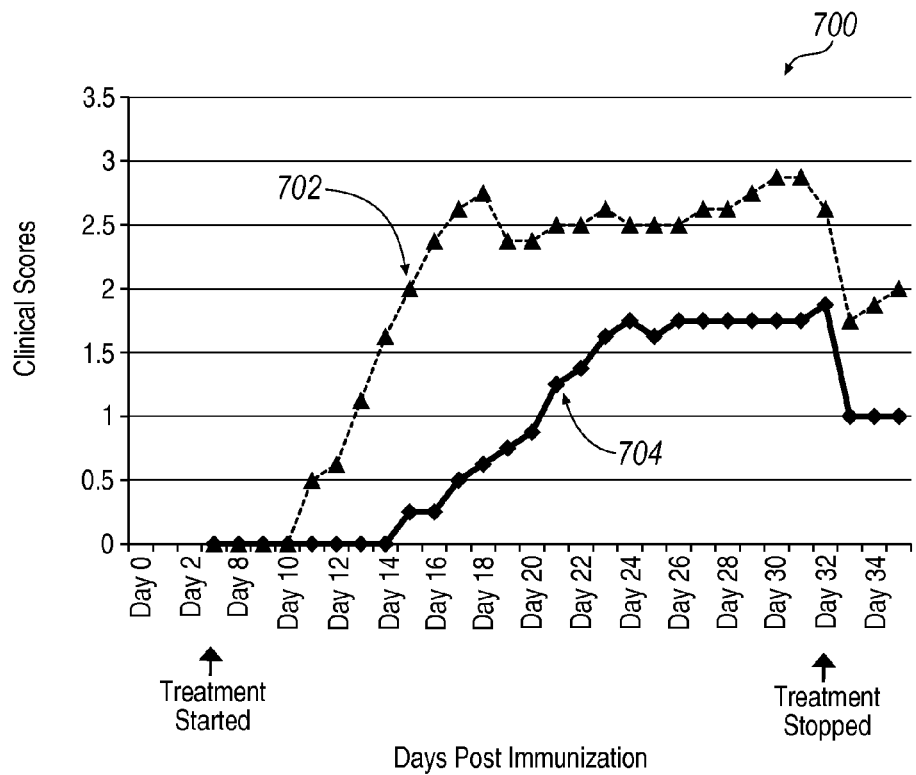
FIG. 15 is a graph showing scores for a control/EAE, and for treatment with 950 nm IRL in a multiple sclerosis (MS) animal model study.

As shown in FIG. 15, graph 700 shows scores for a control/EAE 702, and for treatment with 950 nm IRL 704. Referring to the lower scores that result from the 950 nm IRL treatment, it is clear that if treatment were prolonged then the treatment effect is continued. The clinical course of EAE was ameliorated during the 3 weeks of treatment compared to controls, demonstrating that this effect was directly related to IRL therapy. Note that the clinical scores improve at some point later during the course of this animal model of MS (compare day 32 to day 33) independent of treatment. The important finding is that IRL treatment 1) delays the onset of disease symptoms and 2) improves the clinical scores even after the onset of symptoms, i.e., it ameliorates the condition and severity of the disease in experimental MS.

Spinal Cord

Spinal cord injury (SCI) is a result of trauma (e.g., due to accidents) or diseases including infections. SCI symptoms vary widely from pain to paralysis. Consequences of SCI depend on the level and extent of injury. Cervical SCI often results in a compromised respiratory system. In most cases, the primary treatment of SCI patients with respiratory insufficiency continues to be with mechanical ventilatory support.

Figure 16:
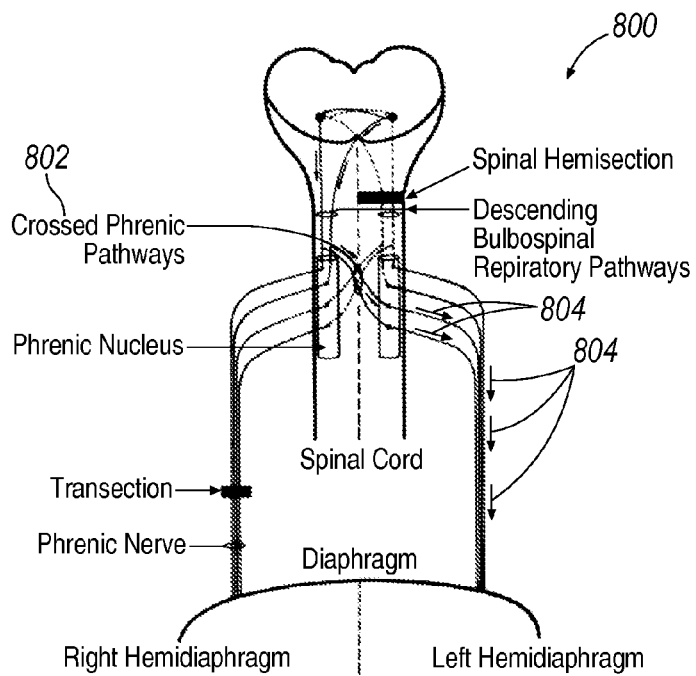
FIG. 16 illustrates a latent respiratory motor pathway can be activated to restore respiratory function to a hemidiaphragm paralyzed by a left C2 hemisection.

In the disclosed model and as illustrated 800 with respect to FIG. 16, a latent respiratory motor pathway can be activated to restore respiratory function to a hemidiaphragm paralyzed by a left C2 hemisection. As a brief description of the model: an upper cervical spinal cord hemisection (C2) interrupts the major descending bulbospinal respiratory pathways and thus paralyzes the ipsilateral hemidiaphragm. However, latent bulbospinal respiratory axons found in the non-damaged regions of the spinal cord can be activated to restore function to a hemidiaphragm paralyzed by ipsilateral C2 hemisection during a reflex known as the "crossed phrenic phenomenon" (CPP), as shown in FIG. 16 at 802. Transection of the contralateral phrenic nerve induces asphyxia, which increases central respiratory drive and activates the initially latent respiratory axons, reestablishing function to the paralyzed hemidiaphragm.

The CPP can also be pharmacologically activated without the need to transect the contralateral phrenic nerve. With the pharmacologic approach, the animal is better able to deal with respiratory distress. According to the disclosed approach, respiratory function is induced with the use of specific infrared light (IRL) wavelengths that alleviate disease symptoms and improve respiratory dysfunction. The use of IRL has the inherent advantage that it is not invasive and can be applied topically at various periods post injury (acute or chronic).

Surgical procedures were used in the past to induce the crossed phrenic phenomenon (CPP). Inspiratory drive to phrenic motoneurons is mediated by medullary neurons in the rostral division of the ventral respiratory group (rVRG). These neurons project bilaterally to the phrenic nuclei and it has been shown that both the crossed and uncrossed descending bulbospinal pathways have spinal decussating collaterals that project to both phrenic nuclei. Hemisection rostral to the phrenic nucleus interrupts (dotted lines) the descending pathways which results in paralysis of the left hemidiaphragm (i.e., ipsilateral to hemisection). Transection of the contralateral (right) phrenic nerve has been employed to paralyze the right hemidiaphragm, induce asphyxia and thus the CPP in many mammalian species. Arrows 804 indicate the pathways followed by respiratory impulses during the CPP to restore function to the hemidiaphragm paralyzed by the SCI.

It is demonstrated that in the C2 hemisection model (C2H), application of IRL can restore respiratory function to a hemidiaphragm paralyzed by C2 hemisection. In this study two hypothses were tested: (1) the hypothesis that IRL application can restore function after a brief (1 h) period of application, and (2) the hypothesis that IRL can restore function in a stimulus intensity-related manner. IRL treatment (870 nm) was applied to separate groups of rats, at a distance of 2 cm from the shaved spinal cord with a diode power output of 200 mW/cm$^2$, and started directly after completion of surgery for the indicated durations.

Experimental Design: Parameter 1

First parameter of study (1): that IRL application immediately after C2 hemisection for 1 hour only can restore function in C2 hemisected rats. Respiratory function was assessed 24 hours later.

Experiment 1: Assessment of Effects of IRL Applied Immediately After C2 Hemisection on Respiratory-Related Activity in a Hemidiaphragm Paralyzed Injury Experimental Design and controls: Adult female Sprague Dawley rats (250-320 g, n=6 per experimental group) were used. All rats were anesthetized and then subjected to a left C2 hemisection (C2H) as described previously. Immediately after C2 hemisection, C2H rats were properly prepared in a supine position for IRL topical application for 1 hour only. Appropriate controls (n=3 per group) were classified as (i) SHAM rats subjected to a laminectomy and durotomy only (SH), and (ii) C2H rats not treated with IRL.

At the conclusion of the 1 hour period of IRL exposure, all muscles were sutured and the skin closed with stainless steel wound clips. C2H rats were then placed on a heat-circulating warming blanket to accelerate recovery. To minimize pain, an analgesic (buprenorphine, 0.01-0.05 mg/kg, s.c.) was administered once every 12 hour postop for 24 hours postop. In order to offset dehydration, the rats were injected with 40 cc/kg s.c. saline (0.09%) immediately postop. C2H rats were given water and food ad libitum. Animals were subjected to electromyography (EMG) recordings 24 hours postop as described below.

Experimental Design: Parameter 2: Assessment of Stimulus Intensity-Related Effects of IRL on Respiratory-Related Activity in the Hemidiaphragm of C2H Rats To test the hypothesis that IRL application immediately after C2 hemisection for 2 or 3 hour can restore function in C2H rats in a stimulus-dependent manner.

Experiment 2: Assessment of Stimulus Intensity-Related Effects of IRL on Respiratory-Related Activity in the Hemidiaphragm Paralyzed in C2H Rats Experimental Design and Controls: Adult female Sprague-Dawley rats were prepared as described above. Two groups of C2H were tested with IRL for 2 or 3 hours immediately after C2 hemisection. Level of anesthesia was monitored continuously as previously described. Appropriate controls were classified as described above in Experiment 1. Assessment of respiratory activity was similarly conducted by EMG recordings 24 hour later in control and treatment groups.

Electromyography (EMG) Recordings: All control and C2H rats treated with IRL were assessed for respiratory activity. Animals were re-anesthetized and a horizontal incision made across the abdomen at the base of the rib cage to expose the abdominal surface of the diaphragm under spontaneously-breathing conditions. A sterile pair of platinum electrodes was then inserted into the crural region of each diaphragm to record activity. Recordings were filtered (band width 0.1-3 kHz), amplified and displayed in line with CED 1401 data acquisition system.

Figure 17:
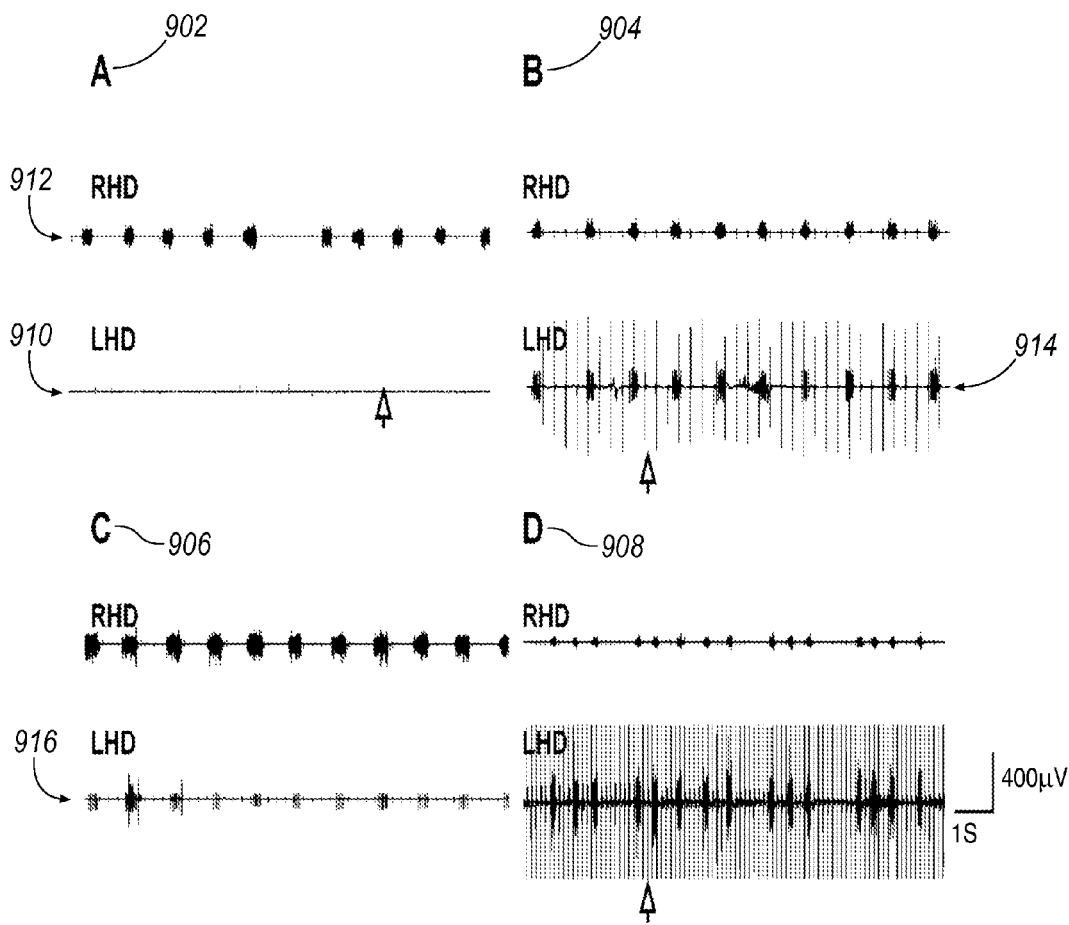
FIG. 17 includes four sets of graphs illustrating accelerated functional recovery after C2 hemisection.

FIG. 17 includes four sets of graphs A, B, C, and D, referred to below respectively as graphs 902, 904, 906, and 908, discussed below in the context of the results.

In C2H rats, EMG recordings show that injury at the cervical (C2) level paralyzed the hemidiaphragm on the same side as the injury. This is shown in Graph A (lower tracing 910) and is the criterion for a functionally-complete hemisection, i.e., a total absence of respiratory-related activity. In contrast, activity in the contralateral hemidiaphragm is evident because it is controlled by the non-injured hemidiaphragm (Graph A, top tracing 912). C2H rats that did not receive any IRL treatment also did not show activity in the paralyzed hemidiaphragm. Following a 1 hour exposure to IRL, respiratory activity in the previously paralyzed hemidiaphragm (Graph B, lower tracing 914) is induced. Compare the lower tracing 914 in Graph B with lower tracing 910 in Graph A. It must be noted that all recording conditions were similar in all experiments. The presence of electrocardiogram (EKG) activity observed as small spikes (e.g., see Graph B, lower tracing 914) are independent of respiratory activity. Detection of EKG activity is expected since all recordings were conducted under spontaneously-breathing conditions.

In Graphs C 906 and D 908, recovery of respiratory activity of the C2H rats is stimulus dependent, i.e., recovered respiratory activity is evident after 2 hours (Graph C) and 3 hours (lower tracing 916) of IRL treatment. As indicated above, the detection of EKG activity is evident and may be related to electrode placement.

The data demonstrates that IRL treatment is a novel approach to induce functional recovery in a hemidiaphragm paralyzed after C2 hemisection. It is shown that functional recovery in the C2H model can occur spontaneously without any intervention 6 weeks after injury, and the extent of recovery induced with IRL is remarkably similar to that observed 6 weeks after injury by spontaneous recovery, suggesting that IRL treatment profoundly accelerates recovery. The current finding with this novel application of IRL is that it offers a unique therapeutic perspective into recovery post paralysis. A key advantage with IRL is that it is noninvasive and therefore carries a minimum amount of risk in clinical applications.

Accordingly, a light therapy method is disclosed that includes identifying a pathological condition in a patient, selecting a light wavelength based on the identified pathological condition, and applying the selected light wavelength, or a combination of the selected light wavelengths, to the patient using a light source. In an alternative expression, a treatment method includes diagnosing a pathological condition in a patient, providing a light source having an array of output lights that include different light wavelengths between 700 nm and 1000 nm, applying, based on the diagnosed pathological condition, one or a combination of the light wavelengths to the patient using the light source.

Figure 18:
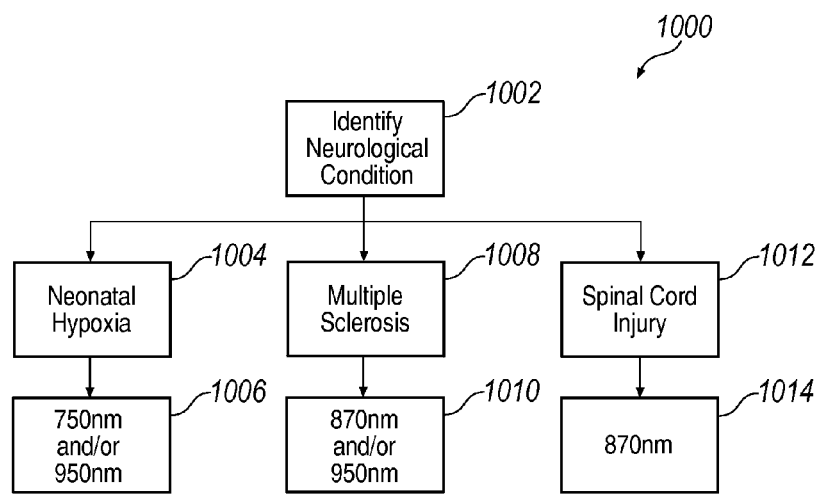
FIG. 18 illustrates an overall summary of above results with respect to neonatal hypoxia, multiple sclerosis (MS), and spinal cord injury.

Referring to FIG. 18, illustration 1000 illustrates an overall summary of above results with respect to neonatal hypoxia, multiple sclerosis (MS), and spinal cord injury, and is not necessarily a decision tree for following treatment. Further, the wavelengths or combinations of wavelengths are examples shown in FIG. 18 based on results of several tests as disclosed above. However, it is contemplated that other wavelengths and combinations of wavelengths that inhibit CcO activity including 750 nm, 870 nm, 900 nm, and 950 nm and their respective ranges may also be used for such treatments as well, according to the disclosure.

Illustration 1000 shows that a neurological condition is identified at step 1002. For neonatal hypoxia 1004, discussion above indicates application of approximately 750 nm and/or approximately 950 nm as effective treatments, 1006. In one example, application of approximately 50 mW/cm$^2$ of infrared power at a distance of approximately 30 cm and delivered proximate to the scalp via a fiber optic, was found to be beneficial when applied to a scalp.

Illustration 1000 shows, for MS 1008, discussion above indicates application of approximately 870 nm and/or approximately 950 nm as effective treatments, 1010. In one example, application of approximately 200 mW/cm$^2$ of infrared power at a distance of approximately 2 cm was found to be beneficial when applied to the head or spinal cord.

Illustration 1000 shows, for a spinal cord injury 1012, discussion above indicates application of approximately 870 nm as effective treatment 1014. In one example, application of approximately 200 mW/cm$^2$ of infrared light power output at a distance of approximately 2 cm was found to be beneficial when applied to the spinal cord after injury.

Accordingly, in one embodiment and referring back to FIG. 8, it is contemplated that light therapy device or source 100 may include lights having wavelengths that fall within ranges of wavelengths of 730-770 nm, 850-890 nm, 880-920 nm, and 930-970 nm, for the treatment of neonatal hypoxia, multiple sclerosis (MS), and spinal cord injury. In one exemplary embodiment a wavelength range of 950-970 nm is applied.

Further, although the above-referenced wavelengths are illustrative of tests conducted and benefits accrued, it is contemplated that other wavelengths and/or combinations of wavelengths apply as well based on the above, and none of such wavelengths or combinations of wavelengths are necessarily excluded. As stated, light with a wavelength within the ranges of approximately 730-770 nm, 850-890 nm, 880-920 nm, or 930-970 nm directly or indirectly inhibits CcO. Thus combinations of two or more wavelengths within the given ranges also may be applied to cause an additive or synergistic benefit.

That is, other wavelengths, alone or in combination, of infrared light may inhibit CcO besides those listed herein. The wavelengths described herein are exemplary and may represent a range of frequencies centered around the frequency disclosed. Thus, reducing reperfusion injury using light may be the result of a synergistic effect caused by the light source outputting a range or spectrum of wavelengths.

Figure 19:
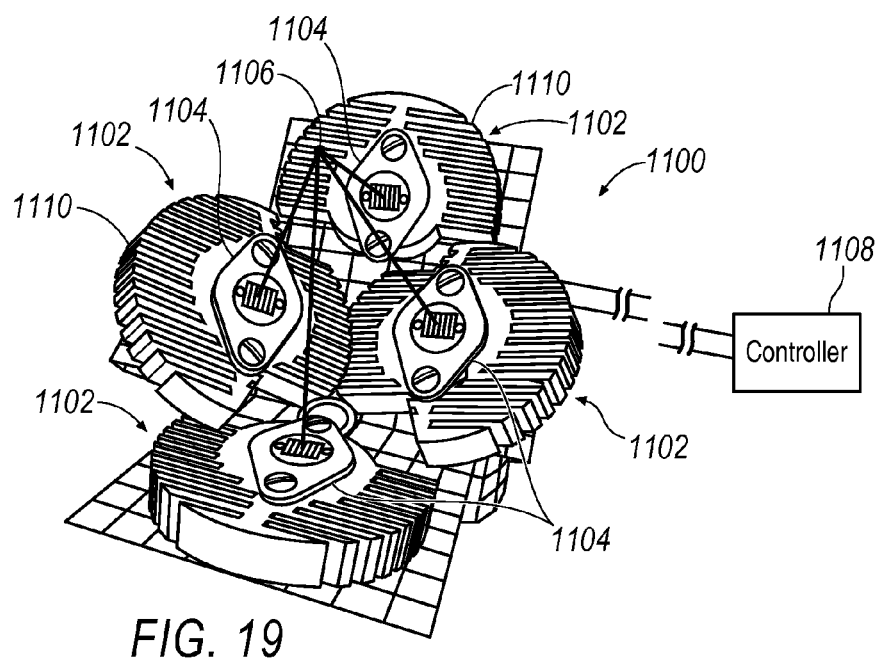
FIGS. 19-21 illustrate exemplary apparatus for selectively delivering light to a patient for treatment.
Figure 20:
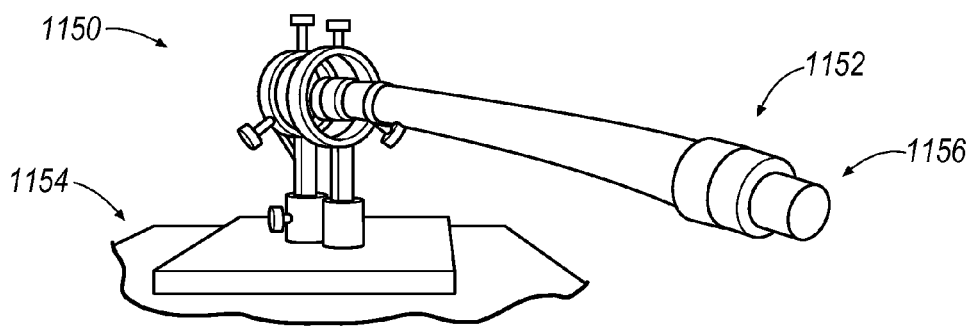
Figure 21:
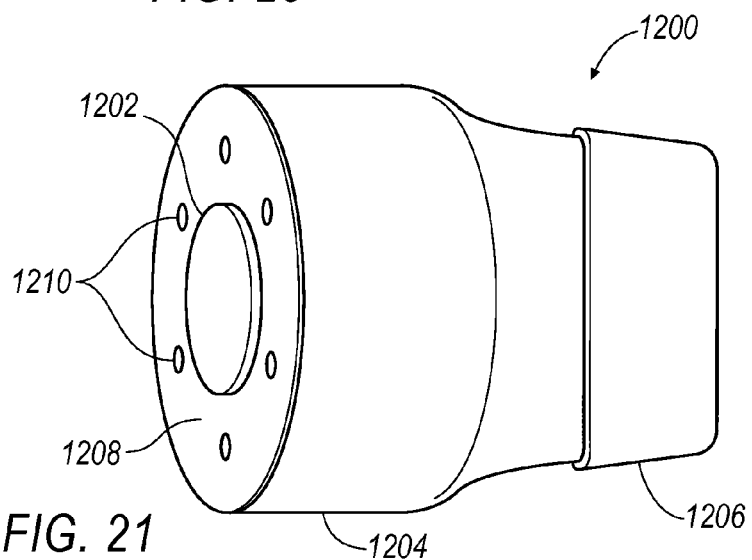

FIGS. 19, 20, and 21 illustrate exemplary apparatus for delivering infrared light.

Apparatus 1100 of FIG. 19, for instance, includes 4 generally planar support structures 1102 applicable for relatively higher power treatments such as up to 5 Watts. Each planar structure 1102 includes a respective diode array 1104, and each diode array 1104 may include a mix of diodes having ranges of 730-770 nm, 850-890 nm, 880-920 nm, and 930-970 nm as described. In such an example, diodes may be individually turned on and off, such that specific ranges of wavelengths may be individually applied (such as, for instance diodes having the range 730-770 nm). In such fashion, any combination of ranges of wavelengths may be applied by selectively applying one or more wavelengths from one or more of the diode arrays 1104.

In another example, diode arrays 1104 may each be dedicated to one of the wavelength ranges 730-770 nm, 850-890 nm, 880-920 nm, and 930-970 nm. Thus, in this example, one of the arrays 1104 may have only diodes having 730-770 nm as a wavelength, another array 1104 may have only diodes having 850-890 nm, one of the arrays 1104 may have only diodes having 880-920 nm as a wavelength, and another array 1104 may have only diodes having 930-970 nm, Further, it is contemplated that each support structure 1102 may be aimed toward a common focal point 1106. In such fashion, apparatus 1100 may be manipulated, with individual diodes within arrays 1104 and controllable by a controller 1108, such that focal point 1106 may be positioned on a patient or proximate a patient for optimal wavelength delivery for treatment. Each structure 1102 also includes, in the illustrated example, heat transfer fins 1110 that serve to assist in transferring heat from diode arrays 1104 during operation, to prevent self-overheating, as well as avoiding injury to a patient due to radiative or convective heat from the hot diode arrays 1104.

According to another exemplary embodiment, an apparatus 1150 illustrated in FIG. 20 includes a fiber optic light guide 1152 that is supported by a support structure 1154. Apparatus 1150 is thereby positionable such that one or more diodes may be positioned at an input end, the light being guided down light guide 1152 to an outlet end 1156, such that light can be selectively delivered while having the diode(s) positioned at a distance. In such fashion, the light can be guided and positioned readily and without having the diode(s) proximate the patient, thus avoiding injury to a patient due to radiative or convective heat from the hot diode(s). A controller, such as controller 1108 of FIG. 19, may likewise be arranged to selectively operate the diode(s). Apparatus 1150 may be applicable for more directed treatments, such as for neonates, such that wavelength(s) can be directed toward very specific areas.

According to another exemplary embodiment, an apparatus 1200 illustrated in FIG. 21 includes one or more diodes 1202 positioned on a heat sink 1204. A fan 1206 is positioned at an end of apparatus 1200 that is opposite the one or more diodes 1202. The one or more diodes 1202 may be positioned on a plate 1208 having perforations 1210, such that air flow may be caused to pass within apparatus 1200, passing into perforations 1210 and through cavities (not shown) within heat sink 1204, cooling the one or more diodes 1202 to prevent self-overheating, as well as avoiding injury to a patient due to radiative or convective heat from the hot one or more diodes 1202. A controller, such as controller 1108 of FIG. 19, may likewise be arranged to selectively operate the diode(s). Apparatus 1200 may be used for high power applications, such as 5 Watts or even more, as the combination of heat sink 1204 with fan 1206 direct air and heat away from the diode and in a direction opposite from a patient receiving treatment.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope of the disclosure should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the disclosure is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A light therapy method, comprising:
   identifying a condition in a tissue of a patient that causes an ischemic event to occur in the tissue;
   selecting at least one light wavelength based on the identified condition; and
   applying one or a combination of the selected light wavelengths to the patient as an amount of light using a light source;
   wherein the step of applying one or a combination of the selected light wavelengths occurs during an onset of reoxygenation of the tissue; and
   wherein applying the one or the combination of the selected light wavelengths begins prior to the onset of reoxygenation of the tissue.

2. The method of claim 1, wherein:
   identifying the condition comprises identifying neonatal hypoxia; and
   applying the one or the combination of the selected light wavelengths comprises applying to a scalp of the patient using the light source.

3. The method of claim 2, wherein applying the one or the combination of the selected light wavelengths further comprises applying the one or the combination of the selected light wavelengths that includes one of approximately 750 nm and approximately 950 nm.

4. The method of claim 3, further comprising applying up to approximately 5 W/cm² of infrared light power.

5. The method of claim 1, wherein:
   identifying the condition comprises identifying a pathological condition that includes multiple sclerosis; and
   applying the one or the combination of the selected light wavelengths comprises applying to one of the head and spinal cord.

6. The method of claim 5, wherein applying the one or the combination of the selected light wavelengths further comprises applying the one or the combination of the selected light wavelengths that includes one of approximately 870 nm and approximately 950 nm.

7. The method of claim 6, further comprising applying up to approximately 5 W/cm² of infrared light power output.

8. The method of claim 1, wherein:
   identifying the condition comprises identifying a pathological condition that includes a spinal cord injury; and
   applying the one or the combination of the selected light wavelengths comprises applying to the spinal cord.

9. The method of claim 8, wherein applying the one or the combination of the selected light wavelengths further comprises applying the one or the combination of the selected light wavelengths that includes approximately 870 nm.

10. The method of claim 9, further comprising applying up to approximately 5 W/cm² of infrared power.

11. The method of claim 1, wherein the light source comprises lights having wavelengths that fall within ranges of wavelengths of at least one of 730-770 nm, 850-890 nm, 880-920 nm, and 930-970 nm.

12. The method of claim 1, wherein applying the one or the combination of the selected light wavelengths begins prior to an initiation of a clinical intervention.

13. The method of claim 12, wherein the clinical intervention includes one of administering a clot-busting drug, inflating or deflating an angioplasty balloon, resuscitation, transfusion, and administering vaso-active drugs.

14. The method of claim 1, further comprising applying the one or the combination of the selected light wavelengths during the reoxygenation of the tissue.

15. The method of claim 1, further comprising applying the one or the combination of the selected light wavelengths after an initiation of a clinical intervention.

16. The method of claim 15, wherein the clinical intervention includes one of administering a clot-busting drug, inflating or deflating an angioplasty balloon, resuscitation, transfusion, and administering vaso-active drugs.

17. The method of claim 1, further comprising selectively reducing the amount of light being applied to the patient by the light source following the onset of reoxygenation of the tissue.

18. The method of claim 17, wherein the amount of light being applied to the patient is selectively reduced by selectively disabling the light source at different times.

19. The method of claim 17, wherein the amount of light being applied to the patient is selectively reduced by selectively disabling discrete groups of lights within the light source at different times.

20. The method of claim 17, wherein the amount of light being applied to the patient is selectively reduced by moving the light source further away from the patient.

21. The method of claim 1, wherein applying the one or the combination of the selected light wavelengths further comprises applying a light wavelength of approximately 930-970 nm.

22. A treatment method, comprising:
diagnosing a condition in a tissue of a patient that results in an ischemic event to occur in the tissue;
providing an amount of light from a light source having an array of output lights that include different light wavelengths between 700 nm and 1000 nm;
applying, based on the diagnosed condition, one or a combination of light wavelengths to the patient using the light source, during an onset of reperfusion; and
selectively reducing the amount of light being applied to the patient by the light source following an onset of reoxygenation of the tissue;
wherein applying the one or the combination of light wavelengths begins prior to the onset of reoxygenation of the tissue.

23. The method of claim 22, wherein:
diagnosing the condition comprises diagnosing a pathological condition that includes neonatal hypoxia; and
applying the one or the combination of light wavelengths comprises applying to a scalp of the patient using the light source.

24. The method of claim 23, wherein applying the one or the combination of light wavelengths further comprises applying the one or the combination of light wavelengths that includes one of approximately 750 nm and approximately 950 nm.

25. The method of claim 24, further comprising applying up to approximately 5 W/cm² of infrared light power.

26. The method of claim 22, wherein:
diagnosing the condition comprises diagnosing a pathological condition that includes multiple sclerosis; and
applying the one or the combination of light wavelengths comprises applying to one of the head and spinal cord.

27. The method of claim 26, wherein applying the one or the combination of light wavelengths further comprises applying the one or the combination of light wavelengths that includes one of approximately 870 nm and approximately 950 nm.

28. The method of claim 27, further comprising applying up to approximately 5 W/cm² of infrared power.

29. The method of claim 22, wherein:
diagnosing the condition comprises diagnosing a pathological condition that includes a spinal cord injury; and
applying the one or the combination of light wavelengths comprises applying to the spinal cord.

30. The method of claim 29, wherein applying the one or the combination of light wavelengths further comprises applying the one or the combination of light wavelengths that includes approximately 870 nm.

31. The method of claim 30, further comprising applying up to approximately 5 W/cm² of infrared power.

32. The method of claim 22, wherein the one or the combination of light wavelengths applied includes a wavelength falling in at least one of a range of approximately 730-770 nm, approximately 850-890 nm, approximately 880-920 nm, and approximately 930-970 nm.

33. The method of claim 22, wherein the amount of light being applied to the patient is selectively reduced by selectively disabling the light source at different times.

34. The method of claim 22, wherein the amount of light being applied to the patient is selectively reduced by selectively disabling discrete groups of lights within the light source at different times.

35. The method of claim 22, wherein the amount of light being applied to the patient is selectively reduced by moving the light source further away from the patient.

36. The method of claim 22, wherein applying the one or the combination of light wavelengths occurs during the onset of reoxygenation of the tissue.

37. The method of claim 22, wherein applying the one or the combination of light wavelengths further comprises applying a light wavelength of approximately 930-970 nm.

38. A light therapy method, comprising:
identifying a pathological condition in a patient that causes ischemia in a tissue of the patient;
selecting at least one light wavelength based on the identified pathological condition; and
applying one or a combination of the selected light wavelengths to the tissue of the patient using an amount of light from a light source;
wherein at least one of the selected light wavelengths falls in a range of 930-970 nm;
wherein applying the one or the combination of the selected light wavelengths begins prior to the onset of reoxygenation of the tissue; and
wherein applying the one or the combination of the selected light wavelengths occurs after an onset of reoxygenation of the tissue.

39. The method of claim 38, wherein applying the one or the combination of the selected light wavelengths begins prior to an initiation of a clinical intervention.

40. The method of claim 39, wherein the clinical intervention includes one of administering a clot-busting drug, inflating or deflating an angioplasty balloon, resuscitation, transfusion, and administering vaso-active drugs.

41. The method of claim 38, further comprising applying the one or the combination of the selected light wavelengths during reoxygenation of the tissue.

42. The method of claim 38, further comprising applying the one or the combination of the selected light wavelengths after an initiation of a clinical intervention.

43. The method of claim 42, wherein the clinical intervention includes one of administering a clot-busting drug, inflating or deflating an angioplasty balloon, resuscitation, transfusion, and administering vaso-active drugs.

44. The method of claim 38, further comprising selectively reducing the amount of light being applied to the patient by the light source following an onset of reoxygenation of the tissue.

45. The method of claim 44, wherein the amount of light being applied to the patient is selectively reduced by selectively disabling the light source at different times.

46. The method of claim 44, wherein the amount of light being applied to the patient is selectively reduced by selectively disabling discrete groups of lights within the light source at different times.

47. The method of claim 44, wherein the amount of light being applied to the patient is selectively reduced by moving the light source further away from the patient.

48. A method of treating an ischemic event in tissue of a subject in need thereof, the method comprising: applying light to a tissue, prior to an onset of reperfusion, the light having wavelengths selected from two or more of the ranges selected from 730-770 nm, 850-890 nm, 880-920 nm, and 930-970 nm, thereby to reduce ischemic reperfusion injury in the tissue of the subject.

49. The method of claim 48, wherein the light applied comprises light having wavelengths in the range of 730-770 nm and 850-890 nm.

50. The method of claim 49, where in the light applied has wavelengths of about 750 nm and about 870 nm.

51. The method of claim 48, wherein the light applied comprises light having wavelengths in the range of 730-770 nm and 930-970 nm.

52. The method of claim 51, where in the light applied has wavelengths of about 750 nm and about 950 nm.

53. The method of claim 48, wherein the light applied does not comprise a wavelength of about 810 nm.

54. The method of claim 48, wherein the light applied has a power density in the range of 200 mW/cm$^2$ to 800 mW/cm$^2$.

55. The method of claim 48, wherein the light applied has a power density of approximately 200 mW/cm$^2$.

56. The method of claim 48, wherein the light applied is generated by one or more light emitting diodes.

57. The method of claim 56, wherein the light emitting diodes produce light having wavelengths of about 750 nm and about 870 nm.

58. The method of claim 56, wherein the light emitting diodes produce light having wavelengths of about 750 nm and about 950 nm.

59. The method of claim 48, wherein the tissue is brain tissue.

60. The method of claim 48, wherein the light is applied to the tissue for at least 2 hours after the onset of reperfusion.

61. A method of treating an ischemic event in tissue of a subject in need thereof, the method comprising: applying light to a tissue, prior to an onset of reperfusion, thereby to reduce ischemic reperfusion injury in the tissue of the subject;
    wherein the light applied is generated by one or more light emitting diodes; and
    wherein the light emitting diodes produce light having wavelengths of:
        about 750 nm and about 870 nm; or
        about 750 nm and about 950 nm.

62. The method of claim 61, wherein the light applied has a power density in the range of 200 mW/cm$^2$ to 800 mW/cm$^2$.

63. The method of claim 61, wherein the light applied has a power density of approximately 200 mW/cm$^2$.

64. The method of claim 61, wherein the tissue is brain tissue.

65. The method of claim 61, wherein the light is applied to the tissue for at least 2 hours after the onset of reperfusion.

66. The method of claim 61, wherein the light emitting diodes produce light having wavelengths of about 750 nm and about 870 nm.

67. The method of claim 61, wherein the light emitting diodes produce light having wavelengths of about 750 nm and about 950 nm.

* * * * *